(12) United States Patent
Chancey

(10) Patent No.: US 12,102,684 B2
(45) Date of Patent: *Oct. 1, 2024

(54) METHODS OF MAKING AND USING POLYPHENOLS COMPLEXED WITH A PROTEIN, PEPTIDE, AMINO ACID, POLYSACCHARIDE, DISACCHARIDE, OR MONOSACCHARIDE

(71) Applicant: John Robert Chancey, Edmond, OK (US)

(72) Inventor: John Robert Chancey, Edmond, OK (US)

(*) Notice: Subject to any disclaimer, the term of this patent is extended or adjusted under 35 U.S.C. 154(b) by 0 days.

This patent is subject to a terminal disclaimer.

(21) Appl. No.: 17/510,691

(22) Filed: Oct. 26, 2021

(65) Prior Publication Data

US 2022/0047707 A1    Feb. 17, 2022

Related U.S. Application Data

(62) Division of application No. 15/819,305, filed on Nov. 21, 2017, now Pat. No. 11,185,591.

(60) Provisional application No. 62/425,988, filed on Nov. 23, 2016.

(51) Int. Cl.

| | | |
|---|---|---|
| A61K 31/05 | (2006.01) |
| A23L 29/00 | (2016.01) |
| A23L 33/105 | (2016.01) |
| A23L 33/185 | (2016.01) |
| A23L 33/19 | (2016.01) |
| A61K 9/00 | (2006.01) |
| A61K 9/14 | (2006.01) |
| A61K 31/12 | (2006.01) |
| A61K 31/357 | (2006.01) |
| A61K 36/00 | (2006.01) |
| A61K 36/28 | (2006.01) |
| A61K 36/82 | (2006.01) |
| A61K 36/87 | (2006.01) |
| A61K 36/9066 | (2006.01) |
| A61K 47/20 | (2006.01) |
| A61K 47/26 | (2006.01) |
| A61K 47/36 | (2006.01) |
| A61K 47/46 | (2006.01) |

(52) U.S. Cl.
CPC .............. *A61K 47/46* (2013.01); *A23L 29/03* (2016.08); *A23L 33/105* (2016.08); *A23L 33/185* (2016.08); *A23L 33/19* (2016.08); *A61K 9/0053* (2013.01); *A61K 9/145* (2013.01); *A61K 9/146* (2013.01); *A61K 31/05* (2013.01); *A61K 31/12* (2013.01); *A61K 31/357* (2013.01); *A61K 36/28* (2013.01); *A61K 36/82* (2013.01); *A61K 36/87* (2013.01); *A61K 36/9066* (2013.01); *A61K 47/20* (2013.01); *A61K 47/26* (2013.01); *A61K 47/36* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 11,185,591 B2* | 11/2021 | Chancey | ............... | A61K 38/018 |
| 2009/0082738 A1* | 3/2009 | Vad | .................... | A61K 31/7008 |
| | | | | 424/766 |
| 2018/0110861 A1* | 4/2018 | Panda | .................... | C07C 229/08 |

* cited by examiner

*Primary Examiner* — Aaron J Kosar
*Assistant Examiner* — Randall O Winston
(74) *Attorney, Agent, or Firm* — Singleton Law, PLLC; Chainey P. Singleton

(57) ABSTRACT

The present invention a polyphenol complexes with amino acids, peptides, proteins, glycosaminoglycans, polysaccharides, mucopolysaccharide, disaccharides, monosaccharides, amino sugars, glycol-proteins, DNA/RNA oligonucleotides, mRNA, siRNA, antibodies or other micro- or macro biomolecules.

5 Claims, No Drawings

METHODS OF MAKING AND USING POLYPHENOLS COMPLEXED WITH A PROTEIN, PEPTIDE, AMINO ACID, POLYSACCHARIDE, DISACCHARIDE, OR MONOSACCHARIDE

CROSS-REFERENCE TO RELATED APPLICATIONS

This application is a Divisional Application of U.S. patent application Ser. No. 15/819,305 filed Nov. 21, 2017, which claims priority based on U.S. Provisional Application Ser. No. 62/425,988, filed Nov. 23, 2016. The contents of each are incorporated by reference in their entirety.

TECHNICAL FIELD OF THE INVENTION

The present invention is in the field of formulations of nutraceuticals, and more specifically, to a polyphenol complexed with a protein, peptide, amino acid, polysaccharide, disaccharide, or monosaccharide used in nutraceuticals.

STATEMENT OF FEDERALLY FUNDED RESEARCH

None.

INCORPORATION-BY-REFERENCE OF MATERIALS FILED ON COMPACT DISC

None.

BACKGROUND OF THE INVENTION

Without limiting the scope of the invention, its background is described in connection with polyphenol complexed with a protein, peptide, amino acid, polysaccharide, disaccharide, or monosaccharide used in nutraceuticals. Today there is a growing public awareness for healthy nourishment that includes daily amounts of required micronutrients such as vitamins, essential fatty acids and antioxidants. One source of this healthy nourishment is nutraceuticals.

SUMMARY OF THE INVENTION

In the present invention a polyphenol (a turmeric extract or a curcuminoid, a grapeseed extract or a resveratrol, a milk thistle extract or silymarin or silibinin, or a green tea extract or EGCG or quercetin) complexes with proteins, peptides, amino acids, polysaccharides, disaccharides, monosaccharides, amino sugars, glycosaminoglycans, glycol-proteins. Also disclosed are methods of preparing a polyphenol complex, comprising obtaining a polyphenol (a turmeric extract or a curcuminoid, a grapeseed extract or a resveratrol, a milk thistle extract or silymarin or silibinin, or green tea extract or EGCG); obtaining a protein; and mixing the polyphenol and the protein in a solvent. Also disclosed are methods of treating a subject, the method comprising identifying a subject in need of treatment of a polyphenol-related disorder, and administering to the subject a nutraceutical composition comprising a polyphenol-protein complex as described. Also disclosed are methods of preparing a polyphenol complex, comprising obtaining a polyphenol; obtaining a peptide; and mixing the polyphenol and the peptide in a solvent. Also disclosed are methods of treating a subject, the method comprising identifying a subject in need of treatment of a polyphenol-related disorder, and administering to the subject a nutraceutical composition comprising a polyphenol-peptide complex as described. Also disclosed are methods of preparing a polyphenol complex, comprising obtaining a polyphenol; obtaining an amino acid; and mixing the polyphenol and the amino acid in a solvent. Also disclosed are methods of treating a subject, the method comprising identifying a subject in need of treatment of a polyphenol-related disorder, and administering to the subject a nutraceutical composition comprising a polyphenol-acid complex as described. Also disclosed are methods of preparing a polyphenol complex, comprising obtaining a polyphenol; obtaining a polysaccharide; and mixing the polyphenol and the polysaccharide in a solvent. Also disclosed are methods of treating a subject, the method comprising identifying a subject in need of treatment of a polyphenol-related disorder, and administering to the subject a nutraceutical composition comprising a polyphenol-polysaccharide complex as described. Also disclosed are methods of preparing a polyphenol complex, comprising obtaining a polyphenol; obtaining a disaccharide; and mixing the polyphenol and the disaccharide in a solvent. Also disclosed are methods of treating a subject, the method comprising identifying a subject in need of treatment of a polyphenol-related disorder, and administering to the subject a nutraceutical composition comprising a polyphenol-disaccharide complex as described. Also disclosed are methods of preparing a polyphenol complex, comprising obtaining a polyphenol; obtaining a monosaccharide; and mixing the polyphenol and the monosaccharide in a solvent. Also disclosed are methods of treating a subject, the method comprising identifying a subject in need of treatment of a polyphenol-related disorder, and administering to the subject a nutraceutical composition comprising a polyphenol-monosaccharide complex as described. Also disclosed are nutraceutical compositions comprising a polyphenol complexed with a protein, peptide, amino acid, polysaccharide, disaccharide, or monosaccharide as described and a pharmaceutically acceptable excipient, diluent, or carrier.

The present invention provided a polyphenol complex comprising a therapeutically effective amount of one or more polyphenols selected from a turmeric extract, a curcumin, a curcuminoid, a grapeseed extract, a resveratrol, a milk thistle extract, a silymarin, a silibinin, a green tea extract, a epigallocatechin gallate and a quercetin; and one or more complexing agents conjugated to a therapeutically effective amount of one or more polyphenols, wherein the one or more complexing agents are selected from proteins, peptides, amino acids, polysaccharides, disaccharides, monosaccharides, amino sugars, glycosaminoglycans, and glycol-proteins, disposed in a pharmaceutically acceptable excipient, diluent, or carrier.

The therapeutically effective amount of one or more polyphenols may be non-covalently conjugated to the complexing agent. The therapeutically effective amount of one or more polyphenols may be 2, 3, 4, 5, 6, or more polyphenols. The proteins may be selected from Whey protein isolate, Egg protein isolate, Oat protein isolate, Hemp protein, Sunflower protein isolate Pea protein isolate, soybean protein isolate, fishmeal, flaxseed and Brown rice protein isolate. The one or more complexing agents may be N-acetylglucosamine, glucosamine sulfate or N-acetylgalactosamine, glucuronic acid, iduronic acid, galactose chondroitin and glucosamine, glycosaminoglycan. The one or more complexing agents may be Cysteine, N-Acetyl cysteine, Methionine, DL methionine, L methionine, Tyrosine, taurine. The one or more complexing agents may be Glutathione. The therapeutically effective amount of one or more polyphenols comprise a turmeric extract and the one or more complexing agents are selected from whey protein isolate, egg protein isolate, oat protein isolate, hemp protein, sunflower protein isolate pea protein isolate, soybean protein isolate, fishmeal, flaxseed, brown rice protein isolate, N-acetylglucosamine, glucosamine sulfate or N-acetylgalactosamine, glucuronic acid, iduronic acid, galactose chondroitin and glucosamine, glycosaminoglycan, Cysteine, N-Acetyl cysteine, Methionine, DL methionine, L methionine, Tyrosine, taurine, Glycose aminoglycans, mucopolysaccharides, polysaccharide, Chondroitin sulfate and Glucosamine sulfate, Glutathione, or a combination thereof. The therapeutically effective amount of one or more polyphenols comprise a curcuminoid and the one or more complexing agents are selected from whey protein isolate, egg protein isolate, oat protein isolate, hemp protein, sunflower protein isolate pea protein isolate, soybean protein isolate, fishmeal, flaxseed, brown rice protein isolate, N-acetylglucosamine, glucosamine sulfate or N-acetylgalactosamine, glucuronic acid, iduronic acid, galactose chondroitin and glucosamine, glycosaminoglycan, Cysteine, N-Acetyl cysteine, Methionine, DL methionine, L methionine, Tyrosine, taurine, Glycose aminoglycans, mucopolysaccharides, polysaccharide, Chondroitin sulfate and Glucosamine sulfate, Glutathione, or a combination thereof. The therapeutically effective amount of one or more polyphenols comprise a resveratrol and the one or more complexing agents are selected from whey protein isolate, egg protein isolate, oat protein isolate, hemp protein, sunflower protein isolate pea protein isolate, soybean protein isolate, fishmeal, flaxseed, brown rice protein isolate, N-acetylglucosamine, glucosamine sulfate or N-acetylgalactosamine, glucuronic acid, iduronic acid, galactose chondroitin and glucosamine, glycosaminoglycan, Cysteine, N-Acetyl cysteine, Methionine, DL methionine, L methionine, Tyrosine, taurine, Glycose aminoglycans, mucopolysaccharides, polysaccharide, Chondroitin sulfate and Glucosamine sulfate, Glutathione, or a combination thereof. The therapeutically effective amount of one or more polyphenols comprise a silibinin and the one or more complexing agents are selected from whey protein isolate, egg protein isolate, oat protein isolate, hemp protein, sunflower protein isolate pea protein isolate, soybean protein isolate, fishmeal, flaxseed, brown rice protein isolate, N-acetylglucosamine, glucosamine sulfate or N-acetylgalactosamine, glucuronic acid, iduronic acid, galactose chondroitin and glucosamine, glycosaminoglycan, Cysteine, N-Acetyl cysteine, Methionine, DL methionine, L methionine, Tyrosine, taurine, Glycose aminoglycans, mucopolysaccharides, polysaccharide, Chondroitin sulfate and Glucosamine sulfate, Glutathione, or a combination thereof. The therapeutically effective amount of one or more polyphenols comprise Epigallocatechin gallate and the one or more complexing agents are selected from whey protein isolate, egg protein isolate, oat protein isolate, hemp protein, sunflower protein isolate pea protein isolate, soybean protein isolate, fishmeal, flaxseed, brown rice protein isolate, N-acetylglucosamine, glucosamine sulfate or N-acetylgalactosamine, glucuronic acid, iduronic acid, galactose chondroitin and glucosamine, glycosaminoglycan, Cysteine, N-Acetyl cysteine, Methionine, DL methionine, L methionine, Tyrosine, taurine, Glycose aminoglycans, mucopolysaccharides, polysaccharide, Chondroitin sulfate and Glucosamine sulfate, Glutathione, or a combination thereof. The therapeutically effective amount of one or more polyphenols comprise quercetin and the one or more complexing agents are selected from whey protein isolate, egg protein isolate, oat protein isolate, hemp protein, sunflower protein isolate pea protein isolate, soybean protein isolate, fishmeal, flaxseed, brown rice protein isolate, N-acetylglucosamine, glucosamine sulfate or N-acetylgalactosamine, glucuronic acid, iduronic acid, galactose chondroitin and glucosamine, glycosaminoglycan, Cysteine, N-Acetyl cysteine, Methionine, DL methionine, L methionine, Tyrosine, taurine, Glycose aminoglycans, mucopolysaccharides, polysaccharide, Chondroitin sulfate and Glucosamine sulfate, Glutathione, or a combination thereof. The therapeutically effective amount of one or more polyphenols comprise a milk thistle extract and the one or more complexing agents are selected from whey protein isolate, egg protein isolate, oat protein isolate, hemp protein, sunflower protein isolate pea protein isolate, soybean protein isolate, fishmeal, flaxseed, brown rice protein isolate, N-acetylglucosamine, glucosamine sulfate or N-acetylgalactosamine, glucuronic acid, iduronic acid, galactose chondroitin and glucosamine, glycosaminoglycan, Cysteine, N-Acetyl cysteine, Methionine, DL methionine, L methionine, Tyrosine, taurine, Glycose aminoglycans, mucopolysaccharides, polysaccharide, Chondroitin sulfate and Glucosamine sulfate, Glutathione, or a combination thereof.

The present invention provides a nutraceutical composition comprising a therapeutically effective amount of one or more polyphenols selected from a turmeric extract, a curcumin, a curcuminoid, a grapeseed extract, a resveratrol, a milk thistle extract, a silymarin, a silibinin, a green tea extract, a epigallocatechin gallate and a quercetin; and one or more complexing agents conjugated to a therapeutically effective amount of one or more polyphenols, wherein the one or more complexing agents are selected from proteins, peptides, amino acids, polysaccharides, disaccharides, monosaccharides, amino sugars, glycosaminoglycans, glycol-proteins disposed in a pharmaceutically acceptable excipient, diluent, or carrier.

The present invention provides a method of treating a subject suffering from a polyphenol-related disorder comprising the steps of: identifying a subject in need of treatment of a polyphenol-related disorder; and administering to the subject a nutraceutical composition comprising a polyphenol-acid complex comprising a therapeutically effective amount of one or more polyphenols selected from a turmeric extract, a curcumin, a curcuminoid, a grapeseed extract, a resveratrol, a milk thistle extract, a silymarin, a silibinin, a green tea extract, a epigallocatechin gallate and a quercetin; and one or more complexing agents conjugated to a therapeutically effective amount of one or more polyphenols, wherein the one or more complexing agents are selected from proteins, peptides, amino acids, polysaccharides, disaccharides, monosaccharides, amino sugars, glycosaminoglycans, glycol-proteins disposed in a pharmaceutically acceptable excipient, diluent, or carrier.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein the term "Conjugation" follows any Conjugation methodology known to the skilled artisan but generally includes the polyphenol being solubilized with a solvent (ethanol, methanol, etc.) under heat ~50° C., pressure, proper pH (depending on polyphenol) and protected from light while mixing/solubilizing and the mixture is cooled to warmed temperatures (37-45° C.). The conjugate material (proteins, polysaccharides, etc.) is added and allowed to mix for a period of time. A vacuum is created to lower boiling point and vaporizing the solvent for removal and drying of the material. In some instances, it is possible to combine two polyphenols with a conjugate material, e.g., Curcumin and resveratrol can be mixed and conjugated with polysaccharide, or glucosamine sulfate or chondroitin sulfate or a peptide or an amino acid or a protein; or in another embodiment, curcumin and milk thistle (silymarin and/or silibinin) can be mixed and conjugated with polysaccharide, or glucosamine sulfate or chondroitin sulfate or a peptide or an amino acid or a protein; or in another embodiment, curcumin and green tea (EGCG) can be mixed and conjugated with polysaccharide, or glucosamine sulfate or chondroitin sulfate or a peptide or an amino acid or a protein; or in another embodiment, curcumin and quercetin can be mixed and conjugated with polysaccharide, or glucosamine sulfate or chondroitin sulfate or a peptide or an amino acid or a protein. In some instances, it is possible to combine more than two polyphenols a with conjugate material, e.g., Curcumin, resveratrol and milk thistle (silymarin and/or silibinin) can be mixed and conjugated with a polysaccharide, or glucosamine sulfate or chondroitin sulfate or a peptide or an amino acid or a protein; or in another embodiment, curcumin, green tea (EGCG) and milk thistle (silymarin and/or silibinin) can be mixed and conjugated with a polysaccharide, or glucosamine sulfate or chondroitin sulfate or a peptide or an amino acid or a protein; or in another embodiment, curcumin, resveratrol, green tea (EGCG) and milk thistle (silymarin and/or silibinin) can be mixed and conjugated with a polysaccharide, or glucosamine sulfate or chondroitin sulfate or a peptide or an amino acid or a protein;

As used herein the term "Flavonols" denotes derivatives of flavonoids that use the 2-(3,4-dihydroxyphenyl)-3,5,7-trihydroxy-4H-chromen-4-one skeleton. Quercetin (a polyphenol flavonoid) can be conjugated to proteins, peptides & amino acids including proteins like Whey protein isolate, Egg protein isolate, Oat protein isolate, Hemp protein, Sunflower protein isolate and Brown rice protein isolate; Peptides like Glutathione; Amino acids like Cysteine or Methionine; Conjugated polysaccharides like Glycose aminoglycans (GAG)—mucopolysaccharides, Polysaccharides, Chondroitin sulfate and Glucosamine sulfate.

As used herein the term "Flavonolignans" denotes derivatives of natural phenols composed of a part flavonoid and a part lignan. Milk Thistle (*Silybum marianum*) with active constituents including Sylimarin and silibinin can be conjugated to proteins, peptides & amino acids including proteins like Whey protein isolate, Egg protein isolate, Oat protein isolate, Hemp protein, Sunflower protein isolate and Brown rice protein isolate; Peptides like Glutathione; Amino acids like Cysteine or Methionine; Conjugated polysaccharides like Glycose aminoglycans (GAG)—mucopolysaccharides, Polysaccharide, Chondroitin sulfate and Glucosamine sulfate.

As used herein the term "Curcuminoids" (other polyphenols) denotes derivatives of Turmeric (*Curcuma longa*). A phytopolyphenol pigment isolated from the plant *Curcuma longa*, commonly known as turmeric, with a variety of pharmacologic properties. Curcumin blocks the formation of reactive-oxygen species, possesses anti-inflammatory properties as a result of inhibition of cyclooxygenases (COX) and other enzymes involved in inflammation; and disrupts cell signal transduction by various mechanisms including inhibition of protein kinase C. These effects may play a role in the agent's observed antineoplastic properties, which include inhibition of tumor cell proliferation and suppression of chemically induced carcinogenesis and tumor growth in animal models of cancer. Curcuminoids (including curcumin, bisdemethoxycurcumin, demethoxycurcumin) can be conjugated to proteins, peptides & amino acids including proteins like Whey protein isolate, Egg protein isolate, Oat protein isolate, Hemp protein, Sunflower protein isolate and Brown rice protein isolate; Peptides like Glutathione; Amino acids like Cysteine or Methionine; Conjugated polysaccharides like Glycose aminoglycans (GAG)—mucopolysaccharides, Polysaccharides, Chondroitin sulfate and Glucosamine sulfate.

As used herein the term "polyphenol" denotes a structural class of mainly natural, but also synthetic or semisynthetic, organic chemicals characterized by the presence of multiples of phenol structural units. The number and characteristics of these phenol structures underlie the unique physical, chemical, and biological properties (e.g., metabolic, toxic, therapeutic, etc.). Examples include (but not limited to) curcumin (curcuminoids), quercetin, resveratrol, Silymarin, silibinin, tannic acid, Epigallocatechin gallate (EGCG), and ellagitannin. The general physical properties include water-insoluble, moderately water-insoluble and moderately water-soluble compounds with molecular weight of 500-4000 Da, >12 phenolic hydroxyl groups, and 5-7 aromatic rings per 1000 Da (these are general ranges and may be ±20% and be within the definition of polyphenol. Examples of polyphenol include but are not limited to and include derivatives thereof: trans-Resveratrol, Curcumin, Quercetin, Silymarin (standardized Milk Thistle extract), and Epigallocatechin gallate (EGCG—standardized Green Tea extract).

As used herein the term "proteins" denotes large biomolecules, or macromolecules, consisting of one or more long chains of amino acid residues and includes natural and synthetic and modified R groups to achieve natural, synthetic or modified amino acids. Proteins include Whey protein isolate, Egg protein isolate, Oat protein isolate, Hemp protein, Sunflower protein isolate and Brown rice protein isolate, Other proteins (variable conjugations), Pea protein isolate, soybean protein isolate, fishmeal & flaxseed. Amino acids include Cysteine & N-Acetyl cysteine, Methionine, DL methionine, L methionine, Tyrosine (no conjugation), taurine and the like. N-Acetyl-L-cysteine is the N-acetyl derivative of cysteine. It is used as a mucolytic agent to reduce the viscosity of mucous secretions. It has also been shown to have antiviral effects in patients with HIV due to inhibition of viral stimulation by reactive oxygen intermediates. Methionine is one of nine essential amino acids in humans (provided by food), Methionine is required for growth and tissue repair. A sulphur-containing amino acid, methionine improves the tone and pliability of skin, hair, and strengthens nails. Involved in many detoxifying processes, sulphur provided by methionine protects cells from pollutants, slows cell aging, and is essential for absorption and bio-availability of selenium and zinc. Methionine chelates heavy metals, such as lead and mercury, aiding their excretion. It also acts as a lipotropic agent and prevents excess fat buildup in the liver.

As used herein the term "peptides" denotes small biomolecules, or macromolecules, consisting of one or more short chains of amino acid residues. The term "peptide" in the context of a "peptide compound" or a "peptide complex" is meant as a compound having at least two amino acids linked together by a peptide bond. In some embodiments, the peptide is an oligopeptide, for example a bipeptide, having two amino acids, a tripeptide, having three amino acids, a 4-mer, 5-mer, and the like. In some embodiments, the peptide is an oligopeptide comprises between 2-20 amino acids. In other embodiments, the peptide is a polypeptide having between 21-100 amino acids. Glutathione is a tripeptide comprised of three amino acids (cysteine, glutamic acid, and glycine) present in most mammalian tissue. Glutathione acts as an antioxidant, a free radical scavenger and a detoxifying agent. Glutathione is also important as a cofactor for the enzyme glutathione peroxidase, in the uptake of amino acids, and in the synthesis of leukotrienes. As a substrate for glutathione S-transferase, this agent reacts with a number of harmful chemical species, such as halides, epoxides and free radicals, to form harmless inactive products. In erythrocytes, these reactions prevent oxidative damage through the reduction of methemoglobin and peroxides. Glutathione is also involved in the formation and maintenance of disulfide bonds in proteins and in the transport of amino acids across cell membranes.

As used herein the term "carrier" denotes a chemical compound that facilitates the incorporation of a compound into cells or tissues. For example, dimethyl sulfoxide (DMSO) is a commonly utilized carrier as it facilitates the uptake of many organic compounds into the cells or tissues of an organism. A common carrier is water, where an aqueous solution of the product of interest is prepared and administered to a subject.

As used herein the term "diluent" denotes chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

In certain embodiments, the same substance can act as a carrier, diluent, or excipient, or have any of the two roles, or have all three roles. Thus, a single additive to the pharmaceutical composition can have multiple functions.

As used herein the term "physiologically acceptable" denotes a carrier or diluent that does not abrogate the biological activity and properties of the compound.

As used herein the term "Stilbenes" denotes an organic compound with the formula $(C_6H_5CH)_2$. Classified as a diarylethene, it features a central ethene double bond substituted with phenyl groups on each carbon atoms of the double bond. Examples include Resveratrol (Trans-resveratrol (98%) and Resveratrol (50% standardized grape seed extract). Resveratrol is a phytoalexin derived from grapes and other food products with antioxidant and potential chemopreventive activities. Resveratrol induces phase II drug-metabolizing enzymes (anti-initiation activity); mediates anti-inflammatory effects and inhibits cyclooxygenase and hydroperoxidase functions (anti-promotion activity); and induces promyelocytic leukemia cell differentiation (anti-progression activity), thereby exhibiting activities in three major steps of carcinogenesis. This agent may inhibit TNF-induced activation of NF-kappaB in a dose- and time-dependent manner. Resveratrol and trans-resveratrol can be conjugated to proteins, peptides & amino acids including proteins like Whey protein isolate, Egg protein isolate, Oat protein isolate, Hemp protein, Sunflower protein isolate and Brown rice protein isolate; Peptides like Glutathione; Amino acids like Cysteine or Methionine; Conjugated polysaccharides like Glycose aminoglycans (GAG)-mucopolysaccharides, Polysaccharides, Chondroitin sulfate and Glucosamine sulfate.

As used herein the term "subject" denotes an animal, preferably a mammal, and most preferably a human, who is the object of treatment, observation or experiment. The mammal may be selected from the group consisting of mice, rats, rabbits, guinea pigs, dogs, cats, sheep, goats, pigs, cows, horses, primates, such as monkeys, chimpanzees, and apes, and humans. Other animals include wildlife (deer, elk, moose, bear, lion, rhinoceros, elephant, etc.), avian (birds, poultry, chicken, turkey, duck, etc.), reptiles (snake, turtle, tortoise, lizard, etc.) and fish (freshwater, saltwater, etc.).

As used herein the term "therapeutically effective amount" denotes an amount of the polyphenol complexed with a protein, peptide, amino acid, polysaccharide, disaccharide or monosaccharide that elicits the biological or medicinal response indicated. This response may occur in a tissue, system, animal or human that is being sought by a researcher, veterinarian, medical doctor or other clinician, and includes alleviation of the symptoms of the disease being treated.

As used herein the term "treat," "treating," "treatment," or any other variation thereof, does not indicate the complete cure from a disorder. Any amelioration of alleviation of the symptoms of a diseases or disorder to any degree, or any increase in the comfort of the subject, is considered treatment.

As used herein the term "Glycosaminoglycans" denotes (GAGs) or mucopolysaccharides are long unbranched polysaccharides consisting of a repeating disaccharide unit. The repeating unit consists of an amino sugar (N-acetylglucosamine, glucosamine sulfate or N-acetylgalactosamine) along with an uronic sugar (glucuronic acid or iduronic acid) or galactose. For example, chondroitin and glucosamine. Chondroitin sulfate is a sulfated glycosaminoglycan (GAG) composed of a chain of alternating sugars (N-acetylgalactosamine and glucuronic acid). It is usually found attached to proteins as part of a proteoglycan. A chondroitin chain can have over 100 individual sugars, each of which can be sulfated in variable positions and quantities. Chondroitin sulfate is an important structural component of cartilage and provides much of its resistance to compression. Glucosamine is commonly used as a treatment for osteoarthritis. It is an amino sugar and a prominent precursor in the biochemical synthesis of glycosylated proteins and lipids. Since glucosamine is a precursor for glycosaminoglycans, and glycosaminoglycans are a major component of joint cartilage, supplemental glucosamine may help to rebuild cartilage and treat arthritis. Other polysaccharides include fucoidan (sulfated polysaccharide) obtained from brown algae and brown seaweed.

As used herein the term "Resveratrol" denotes (3,5,4'-trihydroxy-trans-stilbene or pterostilbene) a stilbenoid, a type of natural phenol, and a phytoalexin produced naturally by several plants in response to injury or when the plant is under attack by pathogens such as bacteria or fungi. Resveratrol is thought to achieve cardioprotective effects by a number of different routes: (1) Inhibition of vascular cell adhesion molecule expression; (2) Inhibition of vascular smooth muscle cell proliferation; (3) Stimulation of endothelial nitric oxide synthase (eNOS) activity; (4) Inhibition of platelet aggregation; and (5) Inhibition of LDL peroxidation. Although trans-Resveratrol is shown below cis-Resveratrol is also considered herein.

As used herein the term "EGCG" denotes Epigallocatechin gallate, also known as epigallocatechin-3-gallate, is the ester of epigallocatechin and gallic acid, and is a type of catechin. Epigallocatechin Gallate is a phenolic antioxidant found in a number of plants such as green and black tea. It inhibits cellular oxidation and prevents free radical damage to cells. EGCG, the most abundant catechin in tea, is a polyphenol.

As used herein the term "Quercetin" denotes a flavonoid widely distributed in nature and is the aglycone form of a number of other flavonoid glycosides, such as rutin and quercetin, found in citrus fruit, buckwheat and onions. Quercetin is a polyphenolic flavonoid with potential chemopreventive activity. Quercetin, ubiquitous in plant food sources and a major bioflavonoid in the human diet, may produce antiproliferative effects resulting from the modulation of either EGFR or estrogen-receptor mediated signal transduction pathways. Although the mechanism of action is not fully known, the following effects have been described with this agent in vitro: decreased expression of mutant p53 protein and p21-ras oncogene, induction of cell cycle arrest at the G1 phase and inhibition of heat shock protein synthesis. This compound also demonstrates synergy and reversal of the multidrug resistance phenotype, when combined with chemotherapeutic drugs, in vitro. Quercetin also produces anti-inflammatory and anti-allergy effects mediated through the inhibition of the lipoxygenase and cyclooxygenase pathways, thereby preventing the production of pro-inflammatory mediators.

As used herein the term "Silymarin" also known as Milk Thistle, denotes a standardized extract of the milk thistle seeds, containing a mixture of flavonolignans consisting of silymarin, silibinin, isosilibinin, silicristin, silidianin, and others. Silibinin is the major active constituent of silymarin, a standardized extract of the milk thistle seeds, containing a mixture of flavonolignans consisting of silibinin, isosilibinin, silicristin, silidianin and others. Silibinin itself is mixture of two diastereomers, silybin A and silybin B, in approximately equimolar ratio. Both in vitro and animal research suggest that silibinin has hepatoprotective (anti-hepatotoxic) properties that protect liver cells against toxins. Silibinin has also demonstrated in vitro anti-cancer effects against human prostate adenocarcinoma cells, estrogen-dependent and -independent human breast carcinoma cells, human ectocervical carcinoma cells, human colon cancer cells, and both small and nonsmall human lung carcinoma cells.

As used herein the term "curcuminoid" denotes a linear diarylheptanoid, with molecules such as curcumin or derivatives of curcumin with different chemical groups that have been formed to increase solubility of curcumins and make them suitable for drug formulation. These compounds are natural phenols and produce a pronounced yellow color. Turmeric extracts or curcuminoids include Curcumin (95% curcuminoids), Curcumin, Desmethoxycurcumin, Bisdesmethoxycurcumin, Tetrahydrocurcumin, Tetrahydrodesmethoxycurcumin, Tetrahydrobisdesmethoxycurcumin and derivatives thereof.

The present inventors have discovered that the ingestion of a polyphenol-protein complex, or polyphenol-peptide complex or polyphenol-amino acid complex or polyphenol-polysaccharide complex or polyphenol-disaccharide or polyphenol-monosaccharide complex significantly increases solubility and the serum bioavailability of the polyphenol as compared to the ingestion of uncomplexed polyphenol.

Thus, in one aspect, disclosed herein are polyphenol-protein complex, or polyphenol-peptide complex or polyphenol-amino acid complex or polyphenol-polysaccharide complex or polyphenol-disaccharide or polyphenol-monosaccharide complex comprising a polyphenol compound linked to a protein compound or peptide compound or an amino acid or a polysaccharide compound or a disaccharide compound or a monosaccharide. In other embodiments, the peptide compound is a protein or a protein fragment. In some embodiments, a protein is naturally occurring and is a full sequence polypeptide expressed by a cell. In other embodiments, a protein is a synthetic protein having a sequence that is not found in nature. In some embodiments, the synthetic protein is expressed by a cell using recombinant technologies, whereas in other embodiments, the synthetic protein is synthesized using a peptide synthesizer. A protein fragment is an oligo- or polypeptide having a sequence identical to a sequence fragment found in a protein.

In some embodiments, the polyphenol compound is linked covalently to a protein compound or peptide compound or an amino acid or a polysaccharide compound or a disaccharide compound or a monosaccharide. In these embodiments, the polyphenol compound is either bound directly to an amino acid of the peptide, or is bound through a linker compound. In some embodiments, the linker is an alkyl, alkenyl, or alkenyl moiety, which may be substituted with a substituent selected from the group consisting of —OH, —SH, —SO, —COOH, —N—C(O)H, —N—C(O)OH, —C(O)NH, and the like. In some embodiment, the linker is bound to the amino acid or the polyphenol compound through a substituent. In other embodiments, the polyphenol compound is linked by hydrogen bonding to the peptide compound to form the complex. In yet other embodiments, the polyphenol compound is linked by electrostatic forces to the protein compound (or peptide compound or an amino acid or a polysaccharide compound or a disaccharide compound or a monosaccharide) to form the complex. In yet other embodiments, the polyphenol compound is linked by lipophilic interactions (e.g., van der Waals forces) to the protein compound (or peptide compound or an amino acid or a polysaccharide compound or a disaccharide compound or a monosaccharide) to form the complex. In some embodiments, the peptide is a full-length protein. In certain embodiments, the protein is one that is found in the serum of a mammal. In other embodiments, the protein is derived from an animal source other than a mammal. In still other embodiment, the protein is derived from plants, such as grains, legumes, fruits, vegetables, and the like.

Examples of oligo- and polypeptides and full-length proteins used in the complexes described herein include, but are not limited to whey protein, tumor necrosis factor (TNF-α); cyclooxygenase (COX) (including COX-1 and COX-2); al-acid glycoprotein (AGP) (also known as orosomucoid); myeloid differentiation protein 2 (MD-2); any one of the group of enzymes called histone acetyl-transferases (HATs), such as p300/CBP; any one of the group of enzymes called histone deacetylases (HDAC); glyoxalase I (GLOI); xanthine oxidase (XO); a proteasome; sarco (endo) plasmic reticulum $Ca^{2+}$ ATPase (SERCA); human immunodeficiency virus type 1 (HIV-1) protease; any one of the DNA methyltransferases (DNMTs), for example DNMT1; DNA polymerase (pol) any one of the ribonucleases (RNases), for example RNase A; any one of the lipoxygenases (LOXs); any one of the matrix metalloproteinases (MMPs); lysozyme; any one of the protein kinase C (PKC) family of enzymes; cellular sarcoma (c-Src); glycogen synthase kinase (GSK)-3β; ErbB2; phosphorylase kinase; any one of the protein reductases, for example thioredoxin reductase (TrxR) and aldose reductase (ALR2); thioredoxin reductase; any one of the caseins; human serum albumin (HSA); bovine serum albumin (BSA); fibrinogen; β-lactoglobulin (β-LG); α-lactalbumin; human serum immunoglobulin (Ig); FtsZ; transthyretin (TTR); glutathione (GSH); and Kelch-like ECH-associated protein 1 (Keap1).

In some embodiments, the polyphenol-protein complex is a complex of polyphenol and whey protein isolate or a brown rice protein isolate. In certain embodiments the polyphenol is a curcuminoid (turmeric extract), or a milk thistle extract (e.g., silymarin and/or silibinin), or a resveratrol, or a green tea extract (e.g., EGCG) or quercetin. In certain embodiments, the whey protein is a milk-derived whey protein or the brown rice protein is a plant derived protein. Milk whey protein is a mixture of 0-lactoglobulin (~65%), α-lactalbumin (~25%), bovine serum albumin (~8%), and immunoglobulins. In some of these embodiments, the complex is formed by mixing the polyphenol and the whey protein isolate in ethanol. Thus, in these embodiments, there is no covalent linkage between the polyphenol and the whey protein. In certain embodiments, the ratio of polyphenol to whey protein or brown rice protein is 1:20 w/w. In other embodiments the ratio of a non-curcuminoid polyphenol to whey protein or brown rice protein is 1:≥40 and 1:≤50 w/w or polyphenol to whey protein or brown rice protein in any increment between 1:>10 and 1:<40. In other embodiments the ratio of non-curcuminoid polyphenol to whey protein or brown rice protein is 1:50 w/w. In some embodiments, the whey protein is obtained from a commercially available source, which comprises 85-90% whey protein in the available powder. In some embodiments, the brown rice protein is obtained from a commercially available source, which comprises 80-90% brown rice protein in the available powder. In some embodiments, the polyphenol is a curcuminoid, or a milk thistle extract (e.g., silymarin and/or silibinin), or a resveratrol, or a green tea extract (e.g., EGCG) or quercetin and is obtained from a commercially available source.

In some embodiments, the polyphenol-protein complex is a complex of polyphenol and sunflower protein or oat protein. In certain embodiments the polyphenol is a curcuminoid (turmeric extract), or a milk thistle extract (e.g., silymarin and/or silibinin), or a resveratrol, or a green tea extract (e.g., EGCG) or quercetin. In certain embodiments, the sunflower protein is a plant derived protein or the oat protein is a plant derived protein. In some of these embodiments, the complex is formed by mixing the polyphenol and the sunflower protein or the oat protein in ethanol. Thus, in these embodiments, there is no covalent linkage between the polyphenol and the sunflower protein or the oat protein. In certain embodiments, the ratio of polyphenol to sunflower protein or oat protein is 1:20 w/w. In other embodiments the ratio of polyphenol to sunflower protein or oat protein is 1:≥40 and 1:≤50 w/w or polyphenol to sunflower protein or oat protein in any increment between 1:>20 and 1:<40. In some embodiments, the sunflower protein is obtained from a commercially available source, which comprises 60-70% sunflower protein in the available powder. In some embodiments, the oat protein is obtained from a commercially available source, which comprises 60-70% oat protein in the available powder. In some embodiments, the polyphenol is a curcuminoid, or a milk thistle extract (e.g., silymarin and/or silibinin), or a resveratrol, or a green tea extract (e.g., EGCG) or quercetin and is obtained from a commercially available source.

In some embodiments, the polyphenol-protein complex is a complex of polyphenol and hemp protein or flaxseed protein. In certain embodiments the polyphenol is a curcuminoid (turmeric extract), or a milk thistle extract (e.g., silymarin and/or silibinin), or a resveratrol, or a green tea extract (e.g., EGCG) or quercetin. In certain embodiments, the hemp protein is a plant derived protein or the flaxseed protein is a plant derived protein. In some of these embodiments, the complex is formed by mixing the polyphenol and the hemp protein or the flaxseed protein in ethanol. Thus, in these embodiments, there is no covalent linkage between the polyphenol and the hemp protein (isolate) or the flaxseed protein (isolate). In certain embodiments, the ratio of polyphenol to hemp protein or flaxseed protein is 1:<100 w/w. In other embodiments the ratio of a polyphenol to hemp protein or flaxseed protein is 1:≥50 and 1:≤100 w/w or polyphenol to hemp protein or flaxseed protein in any increment between 1:>40 and 1:<50. In some embodiments, the hemp protein is obtained from a commercially available source, which comprises 60-70% hemp protein in the available powder. In some embodiments, the flaxseed protein is obtained from a commercially available source, which comprises 60-70% flaxseed protein in the available powder. In some embodiments, the polyphenol is a curcuminoid, or a milk thistle extract (e.g., silymarin and/or silibinin), or a resveratrol, or a green tea extract (e.g., EGCG) or quercetin and is obtained from a commercially available source.

In another aspect, disclosed herein is a nutraceutical composition comprising a polyphenol-peptide complex, as described herein, and a pharmaceutically acceptable carrier, diluent, or excipient. In certain embodiments the polyphenol is a curcuminoid (turmeric extract), or a milk thistle extract (e.g., silymarin and/or silibinin), or a resveratrol, or a green tea extract (e.g., EGCG) or quercetin. In certain embodiments the peptide is a tripeptide. In other embodiments the peptide is glutathione. In some embodiments the glutathione which comprises the three amino acids L-cysteine, L-glutamic acid and glycine is obtained from a commercially available source. The sulfhydryl group of cysteine is primarily responsible for the biological activity of glutathione. As an important antioxidant, glutathione can decrease intracellular damage caused by ROS (reactive oxidative species). In some of these embodiments, the complex is formed by mixing the polyphenol and the glutathione in ethanol. Thus, in these embodiments, there is no covalent linkage between the polyphenol and the glutathione. In certain embodiments, the ratio of polyphenol to glutathione is 1:<10 w/w. In other embodiments the ratio of a polyphenol glutathione is 1:≥10 and 1:≤20 w/w or polyphenol to glutathione in any increment between 1:≥1 and 1:≤20.

In another aspect, disclosed herein is a nutraceutical composition comprising a polyphenol-amino acid complex, as described herein, and a pharmaceutically acceptable carrier, diluent, or excipient. In certain embodiments the polyphenol is a curcuminoid (turmeric extract), or a milk thistle extract (e.g., silymarin and/or silibinin), or a resveratrol, or a green tea extract (e.g., EGCG) or quercetin. In certain embodiments the amino acid is cysteine. In other embodiments the cysteine amino acid is N-Acetyl-cysteine and is available from a commercially available source. N-acetyl cysteine is a white crystalline powder with a slight odor and sour taste. N-acetyl-cysteine is soluble in water and ethanol. N-acetyl-cysteine molecular formula is $C_5H_9NO_3S$ and a molecular weight of 163.191 g/mol. The sulfhydryl group of cysteine is primarily responsible for the biological activity of N-acetyl-cysteine. In some embodiments the amino acid is methionine. In other embodiments the methionine is DL-methionine or N-acetyl-DL-methionine or L-methionine or D-methionine and is available from a commercially available source. The molecular formula for DL-methionine is $C_4H_{11}NO_2S$ and the molecular weight is 149.208 g/mol. Methionine is an essential amino acid required for growth and tissue repair. In some of these embodiments, the complex is formed by mixing the polyphenol and the amino acid, n-acetyl-cysteine or DL-methionine, in ethanol. Thus, in these embodiments, there is no covalent linkage between the polyphenol and the amino acid n-acetyl-cysteine or DL-methionine. In certain embodiments, the ratio of polyphenol to N-acetyl-cysteine or DL-methionine is 1:1, 1:2, 1:4 or 1:≤10 w/w. In other embodiments the ratio of a polyphenol to N-acetyl-cysteine or DL-methionine is 1:≥10 and 1:≤20 w/w or polyphenol to N-acetyl-cysteine or DL-methionine in any increment between 1:≥1 and 1:≤20.

In other embodiments, disclosed herein include a nutraceutical composition comprising a polyphenol-disaccharide complex, as described herein, and a pharmaceutically acceptable carrier, diluent, or excipient. In certain embodiments the polyphenol is a curcuminoid (turmeric extract), or a milk thistle extract (e.g., silymarin and/or silibinin), or a resveratrol, or a green tea extract (e.g., EGCG) or quercetin. In certain embodiments the disaccharide is chondroitin. In other embodiments chondroitin is chondroitin sulfate and is an animal or plant derived mucopolysaccharide or glycosaminoglycan and is available from a commercially available source. Chondroitin sulfate is a white powder and soluble in water and ethanol. Chondroitin sulfate molecular formula is $C_{13}H_{21}NO_{15}S$ and a molecular weight of 463.363 g/mol. In some of these embodiments, the complex is formed by mixing the polyphenol and the chondroitin sulfate in ethanol. Thus, in these embodiments, there is no covalent linkage between the polyphenol and chondroitin sulfate. In certain embodiments, the ratio of polyphenol to chondroitin sulfate is 1:1, 1:2, 1:4 or 1:≤10 w/w. In other embodiments the ratio of a polyphenol to chondroitin sulfate is 1:≥10 and 1:≤20 w/w or the ratio of a polyphenol to chondroitin sulfate in any increment between 1:≥1 and 1:≤20.

In other embodiments, disclosed herein include a nutraceutical composition comprising a polyphenol-monosaccharide complex, as described herein, and a pharmaceutically acceptable carrier, diluent, or excipient. In certain embodiments the polyphenol is a curcuminoid (turmeric extract), or a milk thistle extract (e.g., silymarin and/or silibinin), or a resveratrol, or a green tea extract (e.g., EGCG) or quercetin. In certain embodiments the monosaccharide is glucosamine. In other embodiments glucosamine is glucosamine sulfate and is an animal or plant derived monosaccharide and is available from a commercially available source. glucosamine sulfate is a white powder and soluble in water and ethanol. glucosamine sulfate molecular formula is $C_{13}H_{21}NO_{15}S$ and a molecular weight of 463.363 g/mol. In some of these embodiments, the complex is formed by mixing the polyphenol and the glucosamine sulfate in ethanol. Thus, in these embodiments, there is no covalent linkage between the polyphenol and glucosamine sulfate. In certain embodiments, the ratio of polyphenol to glucosamine sulfate is 1:1, 1:2, 1:4 or 1:≤10 w/w. In other embodiments the ratio of a polyphenol to glucosamine sulfate is 1:≥10 and 1:≤20 w/w or the ration of a polyphenol to glucosamine sulfate in any increment between 1:≥1 and 1:≤20.

In another aspect, disclosed herein is a nutraceutical composition comprising a polyphenol complexed with a protein, peptide, amino acid, polysaccharide, disaccharide or monosaccharide, as described herein, and a pharmaceutically acceptable carrier, diluent, or excipient. The nutraceutical compositions disclosed herein may be manufactured in a manner that is itself known, e.g., by means of conventional mixing, dissolving, granulating, dragee-making, levigating, emulsifying, encapsulating, entrapping or tableting processes. Nutraceutical compositions disclosed herein thus may be formulated in conventional manner using one or more physiologically acceptable carriers comprising excipients and auxiliaries which facilitate processing of the polyphenol-peptide complexed with a protein, peptide, amino acid, polysaccharide, disaccharide or monosaccharide into preparations which can be used nutraceutically or as a food ingredient (e.g., drink mixes, chocolate, gummies, granola, soup mixes, etc.). Any of the well-known techniques, carriers, and excipients may be used as suitable and as understood in the art; e.g., in Remington's Pharmaceutical Sciences, above.

For oral administration, the polyphenol complexed with a protein, peptide, amino acid, polysaccharide, disaccharide or monosaccharide can be formulated readily by combining the polyphenol complexed with a protein, peptide, amino acid, polysaccharide, disaccharide or monosaccharide with pharmaceutically acceptable carriers well known in the art. Such carriers enable the presently disclosed complexes to be formulated as tablets, pills, dragees, capsules, liquids, gels, syrups, slurries, suspensions and the like, for oral ingestion by a subject. Nutraceutical preparations for oral use can be obtained by mixing one or more solid excipient with the disclosed polyphenol-peptide complexes, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Nutraceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

Nutraceutical compositions suitable for use in the methods disclosed herein include compositions where the polyphenol-peptide complex is contained in an amount effective to achieve its intended purpose. More specifically, a therapeutically effective amount means an amount of the polyphenol-peptide complex effective to prevent, alleviate or ameliorate symptoms of disease or prolong the survival of the subject being treated.

Typically, the dose range of the polyphenol-complexed with a protein, peptide, amino acid, polysaccharide, disaccharide or monosaccharide administered to the patient is from about 0.5 to 100 mg/kg of the patient's body weight. The dosage may be a single one or a series of two or more given in the course of one or more days, as is needed by the patient. In some embodiments, the dosage is between 0.1 mg to 50 mg. In other embodiments, the dosage is between 1 mg to 10 mg. Other dose ranges include between 10 to 50 mg, between 20 to 50 mg, between 30 to 50 mg, between 40 to 50 mg, between 20 to 40 mg, between 10 to 20 mg, between 10 to 30 mg, between 20 to 30 mg, and between 30 to 40 mg. The dose may also be at 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, or 200 mg. As used above the dosage refers to active agent dosage and cam be in up to 100 mg or 150 mg. In some embodiments, the dosage is 600 mg s.i.d. (once a day). In another embodiment, the polyphenol-complexed with a protein, peptide amino acid, polysaccharide, disaccharide or monosaccharide when given orally, the total dosage is 600-1200 mg per os b.i.d (twice a day) or 600-1200 mg per os t.i.d. (three times a day) or 600-1200 mg per os or 600-1200 mg per os q.i.d. (four times a day)

In another aspect, disclosed herein is a method of treating a disorder, the method comprising identifying a subject in need thereof and administering to the subject a therapeutically effect amount of a polyphenol complex as disclosed herein.

In another aspect, disclosed herein is a method of treating a disorder, the method comprising identifying a subject in need thereof and administering to the subject a therapeutically effect amount of a polyphenol complexed with a protein, peptide, amino acid, polysaccharide, disaccharide or monosaccharide as disclosed herein, where subsequent to the administration, the serum Cmax of polyphenol is >1 ng/ml<2,000 ng/mL. In some embodiments, the serum Cmax of polyphenol is <0.001% of the administered dose of polyphenol. The definition of the pharmacokinetic parameter $C_{max}$ is well-known to those of skill in the art. Briefly, $C_{max}$ is the maximum observed plasma concentration after a dosage administration.

In another aspect, disclosed herein is a method of preparing a polyphenol complexed with a protein, peptide, amino acid, polysaccharide, disaccharide or monosaccharide, as described above, the method comprising obtaining a polyphenol; obtaining a protein; obtaining a peptide; obtaining an amino acid; obtaining a polysaccharide; obtaining a disaccharide; or obtaining a monosaccharide and mixing the polyphenol and the protein or the peptide or the amino acid or the polysaccharide or the disaccharide or the monosaccharide in a solvent. In some embodiments, the solvent is a polar solvent, while in other embodiments, the solvent is an apolar solvent. In some embodiments, the polar solvent is water, whereas in other embodiments, the polar solvent is an alcohol. In some embodiments, the alcohol is ethanol or methanol Example 1: Preparation of polyphenol-Whey Protein Complex. A polyphenol-whey protein complex was prepared for administration to human subjects. The following materials were used: Whey Protein was 90% protein by weight, polyphenol was 95% by weight and 100% ethyl alcohol. Ratio of polyphenol:whey protein of 1:20 w/w. A 0.5% w/v tincture (solution) was prepared by mixing 50 g curcumin powder with 2000 mL ethanol. The mixture was placed on a magnetic stirring hot plate, with a speed setting at medium, and temperature setting at 50° C. for 30 minutes or until solution turned clear. To the resulting solution was added 950 g whey protein isolate powder. The mixture was placed on a rotary evaporator (rotovap) at slow speed (20-30 rpm), having a water bath temperature of 50° C., and low vacuum for 3-4 hours or until the ethanol was evaporated. Alternatively, the mixture was placed in a lyophilizer. The final product was a fine and orange colored powder. The powder re-solubilizes in water with stirring. Alternative method—In a vacuum blender the polyphenol is added to a 2000 ml. solvent (methanol, acetate, ethanol) at the rate of 25 grams per liter. The mixture is blended at 50° C. for 60 minutes or until mixture is clear. 475 grams of whey protein per liter solvent is added and continued mixing at 40° C. for thirty minutes. Low vacuum is applied to remove solvent until dry. Ratio of a single polyphenol:whey protein of 50 mg polyphenol: 1 gm powder or 1:20 w/w. The above procedure was repeated, except with 25 g polyphenol powder and 1000 g brown rice protein isolate powder. A similar product was obtained with a ration of 1:20 w/w of polyphenol to brown rice protein. The above procedure was repeated, except with 25 g polyphenol powder and 1000 g brown rice protein isolate powder. A similar product was obtained with a ration of 1:20 w/w of polyphenol to brown rice protein. The above procedure was repeated, except with g curcumin powder (95%) and 1000 g brown rice protein isolate powder. A similar product was obtained with a ration of 1:20 w/w of polyphenol to brown rice protein Example 2: Administration of polyphenol-Whey protein Complex. Two healthy individuals were administered a single dose of the polyphenol-whey complex, having a ratio of polyphenol:whey of 25 mg: 1 gm w/w. The dosage contained 25 mg of polyphenol. Blood was drawn from each individual at 20 min, 50 min, and 90 min, and the level of serum polyphenol was calculated.

Curcumin-chondroitin, Curcumin-glucosamine, Curcumin-polysaccharide, Resveratrol-peptide, Resveratrol-amino acid, Resveratrol-chondroitin, Resveratrol-glucosamine, Resveratrol-polysaccharide, EGCG-peptide, EGCG-amino acid, EGCG-chondroitin, EGCG-glucosamine, EGCG-polysaccharide, Quercetin-peptide, Quercetin-amino acid, Quercetin-chondroitin, Quercetin-glucosamine, Quercetin-polysaccharide, Silymarin-peptide, Silymarin-amino acid, Silymarin-chondroitin, Silymarin-polysaccharide and Silymarin-glucosamine.

The present invention includes a composition having Curcuminoid-protein conjugates. In this embodiment the protein may be a natural or synthetic protein and may be of any length, e.g., dipeptide, tripeptides, polypeptides, oligopeptides, etc. The peptide may be conjugated to Curcuminoid, where the peptide is an amino acid. The compositions may be made by solvent assisted blending of curcuminoid-protein conjugates, curcuminoid-peptide conjugates and curcuminoid-amino acid conjugates.

The formulations may include the active agent in communication with a polysaccharide, mucopolysaccharide, glycosaminoglycan, disaccharide, monosaccharide or a amino sugar that is synthetic or naturally occurring. For example, the composition may be curcuminoid-glucosamine conjugates, and Curcuminoid-chondroitin conjugates.

The formulations may include the non-curcuminoid polyphenols, resveratrol Conjugates, resveratrol-proteins, resveratrol-peptides, resveratrol-amino acid, resveratrol-polysaccharide, resveratrol-glucosamine, and resveratrol-chondroitin. The process of making these conjugates include solvent assisted blending of resveratrol-protein conjugates, resveratrol-peptide conjugates and resveratrol-amino acid conjugates and examples of the formulation includes 10-250 mg resveratrol per 1 gram peptides, amino acids and/or saccharides. In other instances formulations include 10-50 mg resveratrol per 1 gram protein. These formulations may be used in animal formulations and human formulations.

The formulations may include the non-curcuminoid polyphenols, Epigallocatechin gallate (EGCG-Green Tea extracts) conjugates like EGCG-protein, EGCG-peptides, EGCG-amino acid, EGCG-polysaccharide, EGCG-glucosamine and EGCG-chondroitin. The process of making these conjugates include solvent assisted blending. Examples of the formulation includes 10-100 mg EGCG per 1 gram peptides, or 1 gram n-acetyl-cysteine or 1 gram DL-methionine or 1 gram chondroitin sulfate or 1 gram glucosamine sulfate. In other instances, formulations include 10-50 mg EGCG per 1 gram protein. Theses formulations may be used in animal formulations and human formulations as antioxidant, anti-inflammatory, immune stimulant, etc.

The formulations may include the non-curcuminoid polyphenols, like quercetin conjugates and examples of the formulation include quercetin-protein, Quercetin-peptides, quercetin-amino acid, quercetin-polysaccharide, quercetin-glucosamine or quercetin-chondroitin. The process of making these conjugates include solvent assisted blending of conjugates and examples of the formulation includes 10-250 mg quercetin per 1 gram peptides, or 1 gram n-acetyl-cysteine or 1 gram DL-methionine or 1 gram chondroitin sulfate or 1 gram glucosamine sulfate. In other instances, formulations include 10-50 mg EGCG per 1 gram protein. These formulations may be used in animal formulations and human formulations.

The formulations may include the non-curcuminoid polyphenols, like Silymarin (silibinin) Milk Thistle extract conjugates and examples of the formulation include Silymarin-proteins, Silymarin-peptides, Silymarin-amino acid, Silymarin-polysaccharide, Silymarin-glucosamine and Silymarin-chondroitin. The process of making these conjugates include solvent assisted blending of curcuminoid-conjugates. Theses formulations may be used in animal formulations including human formulations. Examples of the formulation includes 10-250 mg Silymarin per 1 gram peptides, or 1 gram n-acetyl-cysteine or 1 gram DL-methionine or 1 gram chondroitin sulfate or 1 gram glucosamine sulfate. In other instances, formulations include 10-50 mg Silymarin per 1 gram protein. These formulations may be used in animal formulations and human formulations.

In any of the embodiments may include common peptides (proteins) to be used including Proteins like whey, brown rice, egg, hemp protein, flaxseed protein, etc.; Amino acids—cysteine, methionine; saccharides to be used include glucosamine, polysaccharide & chondroitin.

The formulations may include curcumin-chondroitin conjugates, using chondroitin sulfate-mucopolysaccharide (sulfated glycosaminoglycan) which is a white crystalline powder and 247.30 g/mol, chemical formula $C_{14}H_{19}O_{14}S$, with a melting point about 190-194° C., is water soluble having a pH 5.5-7.5 and may come from marine or animal sources. Chondroitin sulfate is produced from enzymatic digestion of bovine poultry, porcine and marine animal cartilaginous tissues. The benefits include as a dietary supplement for joint health since chondroitin sulfate is a major component of cartilage. Loss of chondroitin sulfate from the cartilage is a major cause of osteoarthritis. Methodology/Preparation. curcumin solubility in water is very poor. Organic solvents (methanol, acetone, DMSO, etc.) will increase solubility. An example of the curcumin-chondroitin sulfate complex is prepared using the following materials: Chondroitin sulfate about 99%; Curcumin powder about 95% curcuminoids (Turmeric *longa*) by weight; Silica (or diatomaceous earth) about 100%; Ethanol about 95% ethyl alcohol. The composition is processed by blending/Processing: 50 grams curcumin with 1-liter ethanol is placed in a rotary mixing vessel at room temperature and medium speed (20 rpm) and blended for 2 hours; 500 grams chondroitin sulfate powder and 25 grams silica are added with continued mixing for another 30 minutes; and a low vacuum is generated in the vessel to remove the ethanol solvent. The resulting powder is a fine, slightly crystalline, off-white color and able to solubilize in water. The ratio of curcumin:chondroitin sulfate is 1:10 w/w.

The formulations include curcumin-Glucosamine conjugate using glucosamine sulfate, which is a white crystalline powder with a 277.2496 g/mol and a chemical formula $C_6H_{15}NO_9S$ and a melting point about 192° C. The source may be from Marine (shellfish, crustacean)—primary and fermentation of grains (primarily corn or wheat). It is slightly water soluble. The benefits include as a dietary supplement for joint health. The methodology/preparation of the curcumin-glucosamine sulfate complex is prepared using the following materials: glucosamine sulfate about 99%; curcumin powder about 95% curcuminoids (Turmeric *longa*) by weight; silica (or diatomaceous earth) about 100%; ethanol about 95% ethyl alcohol. The processing is done by blending/processing: 50 grams curcumin with 1-liter ethanol is placed in a rotary mixing vessel at room temperature and medium speed (20 rpm) and blended for 2 hours. 500 grams of glucosamine sulfate powder and 25 grams silica are added with continued mixing for another 30 minutes. A low vacuum is generated in the vessel to remove the ethanol solvent. Resulting powder is a fine, slightly crystalline, off-white color and able to solubilize in water. The ratio of curcumin:glucosamine sulfate is 1:10 w/w.

The formulations include resveratrol formulation conjugates of peptides, proteins, Amino acids, Polysaccharides, mucopolysaccharides, saccharides, chondroitin, glucosamine, Naturally occurring polyphenol, Stilbene class, stilbenoids, trans-resveratrol (3,5,4'-trihydroxy-trans-stilbene), Active form, with a mol. wt. about 228.25, chem. Formula $C_{14}H_{12}O_3$. Other names include trans-3,5,4'-Trihydroxystilbene, Pterostilbene, 3,4',5-Stilbenetriol, trans-Resveratrol, cis-resveratrol, (E)-5-(p-Hydroxystyryl) resorcinol, (E)-5-(4-hydroxystyryl) benzene-1,3-diol, Pterostilbene with a mol. wt.-256.296 and a chem. formula $C_{16}H_{16}O_3$ Synonym (3,5-Dimethyl-resveratrol). Resveratrol has a mol. wt. about 228.243, chem. formula $C_{14}H_{12}O_3$ synonym (3,5, 4'-Trihydroxystilbene). Resveratrol 3-O-glucoside has a mol. wt. about 390.384 and a chem. formula $C_{20}H_{22}O_8$ synonym (Piceid Polydatin). Resveratrol 5-O-glucoside has a mol. wt. of 390.384 with a chem. formula—$C_{20}H_{22}O_8$.

Resveratrol is a stilbene polyphenolic compounds, has cis and trans two configuration, wherein the trans is the stable structure, and the biological activity is broader. It was first discovered that the grapes contained these substances in 1970s, and through years of research and discovery, it was found that resveratrol not just present in grapes, but present in many fruits, plants and nuts. In 1992, resveratrol was first discovered in commercial wine. Studies shows that resveratrol (trans resveratrol) help to protect the body immune system, lower cholesterol, lower blood pressure, boost energy, helps skin look younger and helps burn fat. Other benefits include anti-oxidant, anti-inflammatory effects on acute and chronic inflammation, support cardio vascular system, protect and stimulate the immune system, protect against neurodegenerative diseases, cancer prevention, and weight loss. Sources include grapes (skin), extracts of the root of *Polygonum cuspidatum*, Japanese knotweed, peanuts, cocoa, berries, blueberries, bilberries, and cranberries.

Resveratrol peptide conjugates include dipeptides, tripeptides, polypeptides, oligopeptides, proteins, protein fragments, etc. Examples of protein and peptide sources include animal, plant and synthetic. The methods of preparation includes organic solvents (methanol, acetone, DMSO, etc.) to increase solubility from 0.03 to 16-50 grams/Liter. An example of the resveratrol-whey protein complex is prepared using whey protein about 85-90% protein by weight, resveratrol powder about 98% resveratrol (*Polygonum cuspidatum*) by weight, ethanol about 95% ethyl alcohol. The blending process includes adding 50 grams resveratrol powder with about 1 liter ethanol is placed in a rotary mixing vessel at room temperature and slow speed (15 rpm) and blended for 1 hour, 1 kilogram whey protein is added with continued mixing for another 30 minutes. A low vacuum is generated in the vessel to remove the ethanol solvent and the resulting powder is a fine off-white color and able to solubilize in water. The ratio of resveratrol:whey protein is 1:20 w/w.

Resveratrol-amino acid conjugates include cysteine, methionine, etc. Cysteine is a white crystalline powder with a MW of 121.15 g/mol and the chemical formula $C_3H_7NO_2S$ and a melting point about 240° C. It is available from plant and animal. It is also water soluble and slightly insoluble in ethanol. An example of the resveratrol-cysteine complex is prepared using the following materials: L-cysteine powder about 99%, Resveratrol powder about 98% resveratrol (*Polygonum cuspidatum*) by weight, Silica (or diatomaceous earth) about 100%, ethanol about 95% ethyl alcohol. The processing or blending includes adding 50 grams resveratrol with 1-liter ethanol is placed in a rotary mixing vessel at room temperature and medium speed (20 rpm) and blended for 2 hours. 500 grams cysteine powder and 25 grams silica are added with continued mixing for another 30 minutes. A low vacuum is generated in the vessel to remove the ethanol solvent. The resulting powder is a fine, slightly crystalline, off-white color and able to solubilize in water. The ratio of resveratrol:cysteine is approximately 1:10 w/w.

Resveratrol-chondroitin conjugates use chondroitin sulfate (sulfated glycosaminoglycan) mucopolysaccharide which is a white crystalline powder with a MW of 247.30 g/mol and a chemical formula $C_{14}H_{19}O_{14}S$, melting point of 190-194° C., and is available from animals and marine. It is water soluble and has a ph 5.5-7.5. Chondroitin sulfate is produced from enzymatic digestion of bovine, poultry, porcine and marine animal cartilaginous tissues. The benefits include joint health since chondroitin sulfate is a major component of cartilage. loss of chondroitin sulfate from the cartilage is a major cause of osteoarthritis. Resveratrol has very poor (0.03 grams/liter) solubility in water so organic solvents (methanol, acetone, dmso, etc.) are used to increase solubility (16-50 grams/liter). The resveratrol-chondroitin sulfate complex is prepared using chondroitin sulfate about 99%, resveratrol powder about 98% resveratrol (*Polygonum cuspidatum*) by weight, silica (or diatomaceous earth) about 100%, and ethanol about 95% ethyl alcohol. The processing or blending includes combining 50 grams resveratrol with 1-liter ethanol is placed in a rotary mixing vessel at room temperature and medium speed (20 rpm) and blended for 2 hours and 500 grams chondroitin sulfate powder and 25 grams silica are added with continued mixing for another 30 minutes. A low vacuum is generated in the vessel to remove the ethanol solvent and the resulting powder is a fine, slightly crystalline, off-white color and able to solubilize in water. The ratio of resveratrol:chondroitin sulfate is 1:10 w/w.

The present invention provides resveratrol-glucosamine conjugates using glucosamine sulfate which is a white crystalline powder with a MW of 277.2496 g/mol and a chemical formula $C_6H_{15}NO_9S$ and a melting point of 192° C. Glucosamine can be found in marine (shellfish, crustacean) and fermentation of grains (primarily corn or wheat). It is slightly water soluble and provides benefits like joint health. An example of the resveratrol-glucosamine sulfate complex is prepared using the following materials glucosamine sulfate about 99%, resveratrol powder about 98% resveratrol (*Polygonum cuspidatum*) by weight, silica (or diatomaceous earth) about 100%, ethanol about 95% ethyl alcohol. The processing or blending includes combining 50 grams resveratrol with 1 liter ethanol is placed in a rotary mixing vessel at room temperature and medium speed (20 rpm) and blended for 2 hours and 500 grams glucosamine sulfate powder and 25 grams silica are added with continued mixing for another 30 minutes. A low vacuum is generated in the vessel to remove the ethanol solvent resulting powder is a fine, slightly crystalline, off-white color and able to solubilize in water. The ratio of resveratrol:glucosamine sulfate is 1:10 w/w.

The present invention provides Green tea extracts-EGCG (epi-gallocatechin gallate) conjugates. EGCG is a naturally occurring polyphenol in the catechin family of flavonoids. The primary antioxidant ingredients include green tea catechins (GTC), Epicatechin (EC), Epigallocatechin (EGC), Epicatechin gallate (ECG), and Epigallocatechin (EGCG)—accounts for more than 40% of the total content. EGCG has a molecular weight of 458.372 g/mol. and the chem. formula $C_{22}H_{18}O_{11}$ with a melting point of 218° C. EGCG has a water solubility of 5 mg/ml and an ethanol solubility of 20 mg/ml. EGCG is a bitter, rust (brown-orange) fine powder. Sources include green tea, white tea, black tea, etc. and the benefits include anti-oxidant, anti-inflammatory, inhibits development of some cancers, and inhibits development of diabetes. Examples of EGCG-peptides conjugates include dipeptides, tripeptides, polypeptides, oligopeptides, proteins, protein fragments, etc. from animal, plant and synthetic sources. An example of the resveratrol-whey protein complex is prepared using the following materials: whey protein about 85-90% protein by weight, EGCG powder about 50%, and ethanol about 95% ethyl alcohol. The processing or blending includes combining 25 grams EGCG powder with 1 liter ethanol is placed in a rotary mixing vessel at room temperature and slow speed (15 rpm) and blended for 1 hour and 500 grams whey protein is added with continued mixing for another 30 minutes. A low vacuum is generated in the vessel to remove the ethanol solvent and the resulting powder is a fine off-white color and able to solubilize in water and the ratio of EGCG:whey protein is 1:20 w/w.

EGCG-amino acids conjugates include cysteine, methionine, etc. For example, the cysteine conjugates are available from plants and animals and are a white crystalline powder with a MW of 121.15 g/mol, melting point of about 240° C. and chemical formula $C_3H_7NO_2S$. It is solubility in water and slightly insoluble in ethanol. An example of the EGCG-cysteine complex is prepared using L-cysteine powder about 99%, EGCG powder about 50%, Silica (or diatomaceous earth) about 100%, water (or organic solvent e.g., ethanol 95%). The processing or blending includes combining 50 grams EGCG with 1 liter water is placed in a rotary mixing vessel at room temperature and medium speed (20 rpm) and blended for 2 hours and 500 grams cysteine powder and 25 grams silica are added with continued mixing for another 30 minutes. A low vacuum under mild heating (40° C.) is generated in the vessel to remove the water and results in a fine powder, slightly crystalline, off-white color and able to solubilize in water. The ratio of EGCG:cysteine is approximately 1:10 w/w.

EGCG-chondroitin conjugates are prepared using chondroitin sulfate about 99%, EGCG about 50% by weight, Silica (or diatomaceous earth) about 100%, and Ethanol about 95% ethyl alcohol. The processing or blending includes combining 50 grams EGCG with 1 liter ethanol is placed in a rotary mixing vessel at room temperature and medium speed (20 rpm) and blended for 2 hours and 500 grams chondroitin sulfate powder and 25 grams silica are added with continued mixing for another 30 minutes. A low vacuum is generated in the vessel to remove the ethanol solvent and results in a fine powder, slightly crystalline, off-white color and able to solubilize in water. The ratio of EGCG:chondroitin sulfate is 1:10 w/w.

EGCG-glucosamine conjugates are prepared using glucosamine sulfate about 99%, EGCG-50% by weight, silica (or diatomaceous earth) about 100%, and ethanol about 95% ethyl alcohol. The processing or blending includes combining 50 grams EGCG with 1 liter ethanol is placed in a rotary mixing vessel at room temperature and medium speed (20 rpm) and blended for 2 hours and 500 grams glucosamine sulfate powder and 25 grams silica are added with continued mixing for another 30 minutes. A low vacuum is generated in the vessel to remove the ethanol solvent and results in a fine powder, slightly crystalline, off-white color and able to solubilize in water. The ratio of EGCG:glucosamine sulfate is 1:10 w/w.

The present invention provides milk thistle-silymarin (silibinin) conjugates. Silymarin (silibinin) is a naturally occurring polyphenol. Milk thistle (*Silybum marianum*) has many complex structural components from the Flavonolignan (lignin family) group of polyphenols, e.g., silymarin and silibinin-standardized extract from the seeds of milk thistle has three structural constituents, with silibinin being the most active, silydianin. Silychristin is water insoluble and soluble in organic solvents (e.g., methanol, ethanol, DMSO) having a chem. formula $C_{25}H_{22}O_{10}$ with a Mol. Wt. of 482.44 g/mol and is a light brown (tan) powder. The benefits include antioxidant, anti-inflammatory, inhibits development of some cancers, and/or inhibits hepatotoxicity.

Silymarin (silibinin)-peptide conjugates include dipeptides, tripeptides, polypeptides, oligopeptides, proteins, protein fragments, etc. An example of the silymarin-whey protein complex is prepared using whey protein about 85-90% protein by weight, silymarin (silibinin) about 80% (30%) and ethanol about 95% ethyl alcohol. The processing or blending includes combining 25 grams silymarin powder with 1 liter ethanol is placed in a rotary mixing vessel at room temperature and slow speed (15 rpm) and blended for 1 hour and 500 grams whey protein is added with continued mixing for another 30 minutes. A low vacuum is generated in the vessel to remove the ethanol solvent resulting in a fine light tan color powder and able to solubilize in water. The ratio of silymarin:whey protein is 1:20 w/w.

Silymarin (silibinin)-amino acid conjugates include cysteine, methionine, etc. Silymarin-cysteine complex is prepared using l-cysteine powder about 99%, silymarin (silibinin) about 80% (30%) by wt., silica (or diatomaceous earth) about 100%, and water (or organic solvent—ex. ethanol 95%). The processing or blending includes combining 50 grams silymarin with 1 liter ethanol is placed in a rotary mixing vessel at room temperature and medium speed (20 rpm) and blended for 2 hours and 500 grams N-acetyl-cysteine powder and 100 grams silica are added with continued mixing for another 30 minutes. A low vacuum under mild heating (40° C.) is generated in the vessel to remove the water, results in a powder that is a fine, slightly crystalline, light tan color and able to solubilize in water. The ratio of silymarin:cysteine is approximately 1:10 w/w.

Silymarin-chondroitin sulfate complex is prepared using chondroitin sulfate about 99%, silymarin (silibinin) about 80% (30%) by wt., silica (or diatomaceous earth) about 100%, and ethanol about 95% ethyl alcohol. The processing or blending includes combining 50 grams silymarin with 1 liter ethanol is placed in a rotary mixing vessel at room temperature and medium speed (20 rpm) and blended for 2 hours and 500 grams chondroitin sulfate powder and 50 grams silica are added with continued mixing for another 30 minutes. A low vacuum is generated in the vessel to remove the ethanol solvent, resulting powder that is a fine, slightly crystalline, off-white color and able to solubilize in water. The ratio of silymarin:chondroitin sulfate is 1:10 w/w.

An example of the silymarin-glucosamine sulfate complex is prepared using glucosamine sulfate about 99%, silymarin (silibinin) about 80% (30%) by wt., silica (or diatomaceous earth) about 100% and ethanol about 95% ethyl alcohol. The processing or blending includes combining 50 grams silymarin with 1 liter ethanol is placed in a rotary mixing vessel at room temperature and medium speed (20 rpm) and blended for 2 hours and 500 grams glucosamine sulfate powder and 50 grams silica are added with continued mixing for another 30 minutes. A low vacuum is generated in the vessel to remove the ethanol solvent, resulting in a powder that is a fine, slightly crystalline, off-white color and able to solubilize in water. The ratio of silymarin:glucosamine sulfate is 1:10 w/w.

In another instance, more than one polyphenol may be complexed with a protein, peptide, amino acid, polysaccharide, disaccharide, or monosaccharide using the same methods described above. In some embodiments, the first polyphenol is a curcuminoid and the second polyphenol is a milk thistle extract (80% silymarin, 30% silibinin). The protein is whey protein isolate. Example 1—Preparation of curcumin/milk thistle extract-whey protein isolate complex. A curcumin/milk thistle extract-whey protein isolate complex was prepared for administration to human and animal subjects. The following materials were used: whey protein isolate was 90% protein by weight, curcumin was 95% curcuminoids by weight, milk thistle extract was 80% silymarin (and 30% silibinin) by weight and 100% ethyl alcohol. Ratio of curcumin:milk thistle extract:whey protein isolate is 0.5:0.5:20 w/w. A 0.5% w/v tincture (solution) was prepared by mixing 25 g curcumin powder and 25 gram milk thistle extract powder with 2000 mL ethanol. The mixture was placed on a magnetic stirring hot plate, with a speed setting at medium, and temperature setting at 50° C. for 30 minutes or until solution turned clear. To the resulting solution was added 950 g whey protein isolate powder. The mixture was placed on a rotary evaporator (rotovap) at slow speed (20-30 rpm), having a water bath temperature of 50° C., and low vacuum for 3-4 hours or until the ethanol was evaporated. Alternatively, the mixture was placed in a lyophilizer. The final product was a fine and yellow colored powder. The powder re-solubilizes in water with stirring. Alternative method—In a vacuum blender the curcumin and milk thistle extract are added to a 2000 ml. solvent (ethanol) at the rate of 12.5 grams (each) per liter. The mixture is blended at 50° C. for 60 minutes or until mixture is clear. 475 grams of whey protein per liter solvent is added and continued mixing at 40° C. for thirty minutes. Vacuum is applied to reactor to remove solvent until dry.

In some embodiments, the first polyphenol is a curcuminoid and the second polyphenol is a milk thistle extract (80% silymarin, 30% silibinin). The monosaccharide is glucosamine sulfate. Example 2 –Preparation of curcumin/milk thistle extract-glucosamine sulfate complex. A curcumin/milk thistle extract-glucosamine sulfate complex was prepared for administration to human and animal subjects. The following materials were used: glucosamine sulfate was 99% by weight, curcumin was 95% curcuminoids by weight, milk thistle extract was 80% silymarin (and 30% silibinin) by weight and 100% ethyl alcohol. Ratio of curcumin:milk thistle extract:glucosamine sulfate is 1:1:4 w/w. A 0.5% w/v tincture (solution) was prepared by mixing 200 g curcumin powder and 200 gram milk thistle extract powder with 2000 mL ethanol. The mixture was placed on a magnetic stirring hot plate, with a speed setting at medium, and temperature setting at 50° C. for 30 minutes. To the resulting solution was added 800 g glucosamine sulfate powder. The mixture was placed on a rotary evaporator (rotovap) at slow speed (20-30 rpm), having a water bath temperature of 50° C., and low vacuum for 3-4 hours or until the ethanol was evaporated. Alternatively, the mixture was placed in a lyophilizer. The final product was a crystalline, fine and orange colored powder. The powder re-solubilizes in water with stirring. Alternative method—In a vacuum blender the curcumin and milk thistle extract are added to a 2000 ml. solvent (ethanol) at the rate of 100 grams (each) per liter. The mixture is blended at 50° C. for 60 minutes. 400 grams of glucosamine sulfate per liter solvent is added and continued mixing at 40° C. for thirty minutes. Vacuum is applied to reactor to remove solvent until dry. In another embodiment, using the methodology described above the ratio of curcumin to milk thistle extract to glucosamine sulfate is 1:1:2.

Example 3—Preparation of curcumin/milk thistle extract/resveratrol-glucosamine sulfate complex. A curcumin/milk thistle extract/resveratrol-glucosamine sulfate complex was prepared for administration to human and animal subjects. The following materials were used: glucosamine sulfate was 99% glucosamine sulfate by weight, curcumin was 95% curcuminoids by weight, milk thistle extract was 80% silymarin (and 30% silibinin) by weight, resveratrol as 98% by weight and 100% ethyl alcohol. Ratio of curcumin:milk thistle extract:resveratrol:glucosamine sulfate is 2:2:1:10 w/w. A 0.5% w/v tincture (solution) was prepared by mixing 200 g curcumin powder and 200 gram milk thistle extract powder and 100 grams resveratrol with 2000 mL ethanol. The mixture was placed on a magnetic stirring hot plate, with a speed setting at medium, and temperature setting at 50° C. for 30 minutes. To the resulting solution was added 1000 g glucosamine sulfate powder. The mixture was placed on a rotary evaporator (rotovap) at slow speed (20-30 rpm), having a water bath temperature of 50° C., and low vacuum for 3-4 hours or until the ethanol was evaporated. Alternatively, the mixture was placed in a lyophilizer. The final product was a crystalline, fine and orange colored powder. The powder re-solubilizes in water with stirring. Alternative method—In a vacuum blender the curcumin and milk thistle extract are added to a 2000 ml. solvent (ethanol) at the rate of 100 grams of curcumin, 100 grams milk thistle extract and 50 grams resveratrol per liter. The mixture is blended at 50° C. for 60 minutes. 500 grams of glucosamine sulfate per liter solvent is added and continued mixing at 40° C. for thirty minutes. Vacuum is applied to reactor to remove solvent until dry. In another embodiment, using the methodology described above the ratio of curcumin to milk thistle extract to glucosamine sulfate is 1:1:1:3.

Example 4—Preparation of curcumin/milk thistle extract-N-acetyl-cysteine complex. A curcumin/milk thistle extract-N-acetyl-cysteine complex was prepared for administration to human and animal subjects. The following materials were used: N-acetyl-cysteine was 99% by weight, curcumin was 95% curcuminoids by weight, milk thistle extract was 80% silymarin (and 30% silibinin) by weight and 100% ethyl alcohol. Ratio of curcumin:milk thistle extract:whey protein isolate is 1:1:4 w/w. A 0.5% w/v tincture (solution) was prepared by mixing 200 g curcumin powder and 200 gram milk thistle extract powder with 2000 mL ethanol. The mixture was placed on a magnetic stirring hot plate, with a speed setting at medium, and temperature setting at 50° C. for 30 minutes. To the resulting solution was added 800 g N-acetyl-cysteine powder. The mixture was placed on a rotary evaporator (rotovap) at slow speed (20-30 rpm), having a water bath temperature of 50° C., and low vacuum for 3-4 hours or until the ethanol was evaporated. Alternatively, the mixture was placed in a lyophilizer. The final product was a crystalline, fine and orange colored powder. The powder re-solubilizes in water with stirring. Alternative method—In a vacuum blender the curcumin and milk thistle extract are added to a 2000 ml. solvent (ethanol) at the rate of 100 grams (each) per liter. The mixture is blended at 50° C. for 60 minutes. 400 grams of N-acetyl-cysteine per liter solvent is added and continued mixing at 40° C. for thirty minutes. Vacuum is applied to reactor to remove solvent until dry. In another embodiment, using the methodology described above the ratio of curcumin to milk thistle extract to N-acetyl-cysteine is 1:1:2.

Example 5—Preparation of curcumin/milk thistle extract-DL-methionine complex. A curcumin/milk thistle extract-DL-methionine complex was prepared for administration to human and animal subjects. The following materials were used: DL-methionine was 99% by weight, curcumin was 95% curcuminoids by weight, milk thistle extract was 80% silymarin (and 30% silibinin) by weight and 100% ethyl alcohol. Ratio of curcumin:milk thistle extract:whey protein isolate is 1:1:4 w/w. A 0.5% w/v tincture (solution) was prepared by mixing 200 g curcumin powder and 200 gram milk thistle extract powder with 2000 mL ethanol. The mixture was placed on a magnetic stirring hot plate, with a speed setting at medium, and temperature setting at 50° C. for 30 minutes. To the resulting solution was added 800 g N-acetyl-cysteine powder. The mixture was placed on a rotary evaporator (rotovap) at slow speed (20-30 rpm), having a water bath temperature of 50° C., and low vacuum for 3-4 hours or until the ethanol was evaporated. Alternatively, the mixture was placed in a lyophilizer. The final product was a crystalline, fine and orange colored powder.

The powder re-solubilizes in water with stirring. Alternative method—In a vacuum blender the curcumin and milk thistle extract are added to a 2000 ml. solvent (ethanol) at the rate of 100 grams (each) per liter. The mixture is blended at 50° C. for 60 minutes. 400 grams of DL-methionine per liter solvent is added and continued mixing at 40° C. for thirty minutes. Vacuum is applied to reactor to remove solvent until dry. In another embodiment, using the methodology described above the ratio of curcumin to milk thistle extract to DL-methionine is 1:1:2.

Example 6—Preparation of curcumin/milk thistle extract/resveratrol-N-acetyl-cysteine complex. A curcumin/milk thistle extract/resveratrol-N-acetyl-cysteine complex was prepared for administration to human and animal subjects. The following materials were used: N-acetyl-cysteine was 99% by weight, curcumin was 95% curcuminoids by weight, milk thistle extract was 80% silymarin (and 30% silibinin) by weight, resveratrol as 98% by weight and 100% ethyl alcohol. Ratio of curcumin:milk thistle extract:resveratrol: N-acetyl-cysteine is 2:2:1:10 w/w. A 0.5% w/v tincture (solution) was prepared by mixing 200 g curcumin powder and 200 gram milk thistle extract powder and 100 grams resveratrol with 2000 mL ethanol. The mixture was placed on a magnetic stirring hot plate, with a speed setting at medium, and temperature setting at 50° C. for 30 minutes. To the resulting solution was added 1000 g N-acetyl-cysteine powder. The mixture was placed on a rotary evaporator (rotovap) at slow speed (20-30 rpm), having a water bath temperature of 50° C., and low vacuum for 3-4 hours or until the ethanol was evaporated. Alternatively, the mixture was placed in a lyophilizer. The final product was a crystalline, fine and orange colored powder. The powder re-solubilizes in water with stirring. Alternative method—In a vacuum blender the curcumin and milk thistle extract are added to a 2000 ml. solvent (ethanol) at the rate of 100 grams of curcumin, 100 grams milk thistle extract and 50 grams resveratrol per liter. The mixture is blended at 50° C. for 60 minutes. 500 grams of N-acetyl-cysteine per liter solvent is added and continued mixing at 40° C. for thirty minutes. Vacuum is applied to reactor to remove solvent until dry. In another embodiment, using the methodology described above the ratio of curcumin to milk thistle extract to N-acetyl-cysteine is 1:1:1:3.

Example 7—Preparation of curcumin/milk thistle extract-hemp protein isolate complex. A curcumin/milk thistle extract-whey protein isolate complex was prepared for administration to human and animal subjects. The following materials were used: hemp protein isolate was 70% protein by weight, curcumin was 95% curcuminoids by weight, milk thistle extract was 80% silymarin (and 30% silibinin) by weight and 100% ethyl alcohol. Ratio of curcumin:milk thistle extract:hemp protein isolate is 1:1:100 w/w. A 0.5% w/v tincture (solution) was prepared by mixing 10 grams curcumin powder and 10 grams milk thistle extract powder with 2000 mL ethanol. The mixture was placed on a magnetic stirring hot plate, with a speed setting at medium, and temperature setting at 50° C. for 30 minutes or until solution turned clear. To the resulting solution was added 1000 g hemp protein isolate powder. The mixture was placed on a rotary evaporator (rotovap) at slow speed (20-30 rpm), having a water bath temperature of 50° C., and low vacuum for 3-4 hours or until the ethanol was evaporated. Alternatively, the mixture was placed in a lyophilizer. The final product is a fine and yellow tan colored powder. The powder re-solubilizes in water with stirring. Alternative method—In a vacuum blender the curcumin and milk thistle extract are added to a 2000 ml. solvent (ethanol) at the rate of 5 grams (each) per liter. The mixture is blended at 50° C. for 60 minutes or until mixture is clear. 500 grams of hemp protein isolate per liter solvent is added and continued mixing at 40° C. for thirty minutes. Vacuum is applied to reactor to remove solvent until dry.

Example 7a—In another instance, more than one polyphenol may be complexed with a protein, peptide, amino acid, polysaccharide, disaccharide, or monosaccharide using the same methods described above. In some embodiments, the first polyphenol is a curcuminoid and the second polyphenol is a milk thistle extract (80% silymarin, 30% silibinin). The protein is brown rice protein isolate. Example 7b—Preparation of curcumin/milk thistle extract-brown rice protein isolate complex. A curcumin/milk thistle extract-brown rice protein isolate complex was prepared for administration to human and animal subjects. The following materials were used: brown rice protein isolate was 90% protein by weight, curcumin was 95% curcuminoids by weight, milk thistle extract was 80% silymarin (and 30% silibinin) by weight and 100% ethyl alcohol. Ratio of curcumin:milk thistle extract:brown rice protein isolate is 1:1:40 w/w. A 0.5% w/v tincture (solution) was prepared by mixing 25 g curcumin powder and 25 gram milk thistle extract powder with 2000 mL ethanol. The mixture was placed on a magnetic stirring hot plate, with a speed setting at medium, and temperature setting at 50° C. for 30 minutes or until solution turned clear. To the resulting solution was added 1000 g brown rice protein isolate powder. The mixture was placed on a rotary evaporator (rotovap) at slow speed (20-30 rpm), having a water bath temperature of 50° C., and low vacuum for 3-4 hours or until the ethanol was evaporated. Alternatively, the mixture was placed in a lyophilizer. The final product was a fine and dull yellow colored powder. The powder re-solubilizes in water with stirring. Alternative method—In a vacuum blender the curcumin and milk thistle extract are added to a 2000 ml. solvent (ethanol) at the rate of 12.5 grams (each) per liter. The mixture is blended at 50° C. for 60 minutes or until mixture is clear. 500 grams of brown rice protein per liter solvent is added and continued mixing at 40° C. for thirty minutes. Vacuum is applied to reactor to remove solvent until dry.

Example 8—Preparation of curcumin/resveratrol-whey protein isolate complex. A curcumin/resveratrol extract-whey protein isolate complex was prepared for administration to human and animal subjects. The following materials were used: whey protein isolate was 90% protein by weight, curcumin was 95% curcuminoids by weight, resveratrol was 98% by weight and 100% ethyl alcohol. Ratio of curcumin: resveratrol:whey protein isolate is 1:1:40 w/w. A 0.5% w/v tincture (solution) was prepared by mixing 25 g curcumin powder and 25 gram resveratrol powder with 2000 mL ethanol. The mixture was placed on a magnetic stirring hot plate, with a speed setting at medium, and temperature setting at 50° C. for 30 minutes or until solution turned clear. To the resulting solution was added 1000 g whey protein isolate powder. The mixture was placed on a rotary evaporator (rotovap) at slow speed (20-30 rpm), having a water bath temperature of 50° C., and low vacuum for 3-4 hours or until the ethanol evaporated. Alternatively, the mixture was placed in a lyophilizer. The final product was a fine and yellow colored powder. The powder re-solubilizes in water with stirring. Alternative method—In a vacuum blender the curcumin and resveratrol are added to a 2000 ml. solvent (ethanol) at the rate of 12.5 grams (each) per liter. The mixture is blended at 50° C. for 60 minutes or until mixture is clear. 500 grams of whey protein per liter solvent is added and continued mixing at 40° C. for thirty minutes. Vacuum is applied to reactor to remove solvent until dry.

Example 9—In another instance, more than one polyphenol may be complexed with a protein, peptide, amino acid, polysaccharide, disaccharide, or monosaccharide using the same methods described above. In some embodiments, the first polyphenol is a curcuminoid and the second polyphenol is a resveratrol. The protein is brown rice protein isolate. Example 1—Preparation of curcumin/resveratrol-brown rice protein isolate complex. A curcumin/resveratrol-brown rice protein isolate complex was prepared for administration to human and animal subjects. The following materials were used: brown rice protein isolate was 90% protein by weight, curcumin was 95% curcuminoids by weight, resveratrol by weight and 100% ethyl alcohol. Ratio of curcumin:resveratrol:brown rice protein isolate is 1:1:40 w/w. A 0.5% w/v tincture (solution) was prepared by mixing 25 g curcumin powder and 25 gram resveratrol powder with 2000 mL ethanol. The mixture was placed on a magnetic stirring hot plate, with a speed setting at medium, and temperature setting at 50° C. for 30 minutes or until solution turned clear. To the resulting solution was added 1000 g brown rice protein isolate powder. The mixture was placed on a rotary evaporator (rotovap) at slow speed (20-30 rpm), having a water bath temperature of 50° C., and low vacuum for 3-4 hours or until the ethanol was evaporated. Alternatively, the mixture was placed in a lyophilizer. The final product was a fine and dull yellow colored powder. The powder re-solubilizes in water with stirring. Alternative method—In a vacuum blender the curcumin and resveratrol are added to a 2000 ml. solvent (ethanol) at the rate of 12.5 grams (each) per liter. The mixture is blended at 50° C. for 60 minutes or until mixture is clear. 500 grams of brown rice protein per liter solvent is added and continued mixing at 40° C. for thirty minutes. Vacuum is applied to reactor to remove solvent until dry.

Example 10—Preparation of curcumin/resveratrol-N-acetyl-cysteine complex. A curcumin/resveratrol-N-acetyl-cysteine complex was prepared for administration to human and animal subjects. The following materials were used: N-acetyl-cysteine was 99% by weight, curcumin was 95% curcuminoids by weight, resveratrol by weight and 100% ethyl alcohol. Ratio of curcumin:resveratrol:whey protein isolate is 1:1:4 w/w. A 0.5% w/v tincture (solution) was prepared by mixing 200 g curcumin powder and 200 gram resveratrol powder with 2000 mL ethanol. The mixture was placed on a magnetic stirring hot plate, with a speed setting at medium, and temperature setting at 50° C. for 30 minutes. To the resulting solution was added 800 g N-acetyl-cysteine powder. The mixture was placed on a rotary evaporator (rotovap) at slow speed (20-30 rpm), having a water bath temperature of 50° C., and low vacuum for 3-4 hours or until 90% of the ethanol was evaporated. Alternatively, the mixture was placed in a lyophilizer. The final product was a crystalline, fine and orange colored powder. The powder re-solubilizes in water with stirring. Alternative method—In a vacuum blender the curcumin and resveratrol are added to a 2000 ml. solvent (ethanol) at the rate of 100 grams (each) per liter. The mixture is blended at 50° C. for 60 minutes. 400 grams of N-acetyl-cysteine per liter solvent is added and continued mixing at 40° C. for thirty minutes. Vacuum is applied to reactor to remove solvent until dry. In another embodiment, using the methodology described above the ratio of curcumin to resveratrol to N-acetyl-cysteine is 1:1:2.

Example 11—Preparation of curcumin/resveratrol-glucosamine sulfate complex. A curcumin/resveratrol-glucosamine sulfate complex was prepared for administration to human and animal subjects. The following materials were used: glucosamine sulfate was 99% by weight, curcumin was 95% curcuminoids by weight, resveratrol by weight and 100% ethyl alcohol. Ratio of curcumin:resveratrol:glucosamine sulfate is 1:1:4 w/w. A 0.5% w/v tincture (solution) was prepared by mixing 200 g curcumin powder and 200 gram resveratrol powder with 2000 mL ethanol. The mixture was placed on a magnetic stirring hot plate, with a speed setting at medium, and temperature setting at 50° C. for 30 minutes. To the resulting solution was added 800 g glucosamine sulfate powder. The mixture was placed on a rotary evaporator (rotovap) at slow speed (20-30 rpm), having a water bath temperature of 50° C., and low vacuum for 3-4 hours or until the ethanol was evaporated. Alternatively, the mixture was placed in a lyophilizer. The final product was a crystalline, fine and orange colored powder. The powder re-solubilizes in water with stirring. Alternative method—In a vacuum blender the curcumin and resveratrol are added to a 2000 ml. solvent (ethanol) at the rate of 100 grams (each) per liter. The mixture is blended at 50° C. for 60 minutes. 400 grams of glucosamine sulfate per liter solvent is added and continued mixing at 40° C. for thirty minutes. Vacuum is applied to reactor to remove solvent until dry. In another embodiment, using the methodology described above the ratio of curcumin to resveratrol to glucosamine sulfate is 1:1:2.

Example 12—Preparation of curcumin/milk thistle extract-chondroitin sulfate complex. A curcumin/milk thistle extract-chondroitin sulfate complex was prepared for administration to human and animal subjects. The following materials were used: chondroitin sulfate was 99% by weight, curcumin was 95% curcuminoids by weight, milk thistle extract was 80% silymarin (and 30% silibinin) by weight and 100% ethyl alcohol. Ratio of curcumin:milk thistle extract:chondroitin sulfate is 1:1:4 w/w. A 0.5% w/v tincture (solution) was prepared by mixing 200 g curcumin powder and 200 gram milk thistle extract powder with 2000 mL ethanol. The mixture was placed on a magnetic stirring hot plate, with a speed setting at medium, and temperature setting at 50° C. for 30 minutes. To the resulting solution was added 800 g chondroitin sulfate powder. The mixture was placed on a rotary evaporator (rotovap) at slow speed (20-30 rpm), having a water bath temperature of 50° C., and low vacuum for 3-4 hours or until the ethanol was evaporated. Alternatively, the mixture was placed in a lyophilizer. The final product was a crystalline, fine and orange colored powder. The powder re-solubilizes in water with stirring. Alternative method—In a vacuum blender the curcumin and milk thistle extract are added to a 2000 ml. solvent (ethanol) at the rate of 100 grams (each) per liter. The mixture is blended at 50° C. for 60 minutes. 400 grams of chondroitin sulfate per liter solvent is added and continued mixing at 40° C. for thirty minutes. Vacuum is applied to reactor to remove solvent until dry. In another embodiment, using the methodology described above the ratio of curcumin to milk thistle extract to chondroitin sulfate is 1:1:2.

Example 13—Preparation of curcumin/resveratrol-chondroitin sulfate complex. A curcumin/resveratrol-chondroitin sulfate complex was prepared for administration to human and animal subjects. The following materials were used: chondroitin sulfate was 99% by weight, curcumin was 95% curcuminoids by weight, resveratrol by weight and 100% ethyl alcohol. Ratio of curcumin:resveratrol:chondroitin sulfate is 1:1:4 w/w. A 0.5% w/v tincture (solution) was prepared by mixing 200 g curcumin powder and 200 gram resveratrol powder with 2000 mL ethanol. The mixture was placed on a magnetic stirring hot plate, with a speed setting at medium, and temperature setting at 50° C. for 30 minutes. To the resulting solution was added 800 g chondroitin sulfate powder. The mixture was placed on a rotary evaporator (rotovap) at slow speed (20-30 rpm), having a water bath temperature of 50° C., and low vacuum for 3-4 hours or until the ethanol was evaporated. Alternatively, the mixture was placed in a lyophilizer. The final product was a crystalline, fine and orange colored powder. The powder re-solubilizes in water with stirring. Alternative method—In a vacuum blender the curcumin and milk thistle extract are added to a 2000 ml. solvent (ethanol) at the rate of 100 grams (each) per liter. The mixture is blended at 50° C. for 60 minutes. 400 grams of chondroitin sulfate per liter solvent is added and continued mixing at 40° C. for thirty minutes. Vacuum is applied to reactor to remove solvent until dry. In another embodiment, using the methodology described above the ratio of curcumin to resveratrol to chondroitin sulfate is 1:1:2.

In another instance, more than one polyphenol may be complexed with a protein, peptide, amino acid, polysaccharide, disaccharide, or monosaccharide using the same methods described above. In some embodiments, the first polyphenol is a curcuminoid and the second polyphenol is a milk thistle extract (80% silymarin, 30% silibinin). The protein is egg protein isolate.

Example 14—Preparation of curcumin/milk thistle extract-egg protein isolate complex. A curcumin/milk thistle extract-egg protein isolate complex was prepared for administration to human and animal subjects. The following materials were used: egg protein isolate was 90% protein by weight, curcumin was 95% curcuminoids by weight, milk thistle extract was 80% silymarin (and 30% silibinin) by weight and 100% ethyl alcohol. Ratio of curcumin:milk thistle extract:egg protein isolate is 1:1:40 w/w. A 0.5% w/v tincture (solution) was prepared by mixing 25 g curcumin powder and 25 gram milk thistle extract powder with 2000 mL ethanol. The mixture was placed on a magnetic stirring hot plate, with a speed setting at medium, and temperature setting at 50° C. for 30 minutes or until solution turned clear. To the resulting solution was added 1000 g egg protein isolate powder. The mixture was placed on a rotary evaporator (rotovap) at slow speed (20-30 rpm), having a water bath temperature of 50° C., and low vacuum for 3-4 hours or until the ethanol was evaporated. Alternatively, the mixture was placed in a lyophilizer. The final product was a fine and yellow colored powder. The powder re-solubilizes in water with stirring. Alternative method—In a vacuum blender the curcumin and milk thistle extract are added to a 2000 ml. solvent (ethanol) at the rate of 12.5 grams (each) per liter. The mixture is blended at 50° C. for 60 minutes or until mixture is clear. 500 grams of egg protein per liter solvent is added and continued mixing at 40° C. for thirty minutes. Vacuum is applied to reactor to remove solvent until dry.

Example 15—Preparation of curcumin/resveratrol-egg protein isolate complex. A curcumin/resveratrol extract-egg protein isolate complex was prepared for administration to human and animal subjects. The following materials were used: egg protein isolate was 90% protein by weight, curcumin was 95% curcuminoids by weight, resveratrol was 98% by weight and 100% ethyl alcohol. Ratio of curcumin:resveratrol:egg protein isolate is 1:1:40 w/w. A 0.5% w/v tincture (solution) was prepared by mixing 25 g curcumin powder and 25 gram resveratrol powder with 2000 mL ethanol. The mixture was placed on a magnetic stirring hot plate, with a speed setting at medium, and temperature setting at 50° C. for 30 minutes or until solution turned clear. To the resulting solution was added 1000 g egg protein isolate powder. The mixture was placed on a rotary evaporator (rotovap) at slow speed (20-30 rpm), having a water bath temperature of 50° C., and low vacuum for 3-4 hours or until the ethanol was evaporated. Alternatively, the mixture was placed in a lyophilizer. The final product was a fine and yellow colored powder. The powder re-solubilizes in water with stirring. Alternative method—In a vacuum blender the curcumin and resveratrol are added to a 2000 ml. solvent (ethanol) at the rate of 12.5 grams (each) per liter. The mixture is blended at 50° C. for 60 minutes or until mixture is clear. 500 grams of egg protein per liter solvent is added and continued mixing at 40° C. for thirty minutes. Vacuum is applied to reactor to remove solvent until dry.

Clinical Case Studies—Example 1: A 60 year old male was presented with lower back pain and pain from foot arthritis. The individual suffers from irritable bowel syndrome (IBD). Several different dosages and formulations were given.

| Formulation and Dosage | Effect | Side effects |
| --- | --- | --- |
| 700 mg conjugate once a day orally for one week-<br>150 mg. Curcumin<br>150 mg. Milk thistle<br>50 mg. resveratrol<br>350 mg. glucosamine sulfate | Symptom relief from lower back pain, foot arthritis, and IBD; significant pain relief with normal work activities | Transient headache; sleep disturbance; |
| 1200 mg conjugate twice a day for two weeks-<br>30 mg. Curcumin<br>30 mg. Milk thistle<br>540 mg. Whey protein isolate | Symptom relief from lower back pain, foot arthritis, and IBD; some pain relief with normal work activities | Transient headache; sleep disturbance |
| 700 mg conjugate once a day for one week-<br>150 mg. Curcumin<br>150 mg. Milk thistle<br>50 mg. Resveratrol<br>350 mg N-acetyl-cysteine | Symptom relief from lower back pain, foot arthritis, and IBD; significant pain relief with normal work activities | Transient headache; sleep disturbance; |

Clinical Case Studies—Example 2: A 64 year old male was presented with lymphoma and multi-focal enlarged lymph nodes. The patient was administered 700 mg (350 mg. glucosamine sulfate; 150 mg.curcumin; 150 mg. Milk thistle; 50 resveratrol) conjugate once a day for two weeks. He displayed moderate shrinking of affected lymph nodes after two weeks. Further use of material did not have any further effect. Side effects—none documented Clinical Case Studies—Example 3: A 57 year old male was presented with small multi-focal lipomas. The patient was administered 700 mg (350 mg. glucosamine sulfate; 150 mg.curcumin; 150 mg. Milk thistle; 50 resveratrol) conjugate once a day for two weeks. There was as much as 50% shrinkage in the size of the lipomas. Side effects—transient headache.

Clinical Case Studies—Example 4: A 50 year old male suffers from pain associated with pelvic arthritis from previous injury. The patient was administered 700 mg (350 mg. glucosamine sulfate; 150 mg.curcumin; 150 mg. Milk thistle; 50 resveratrol) conjugate once a day for two weeks. There was significant pain relief after one week. The individual has been able to resume normal day to day activities. Side effects—none noted.

Clinical Case Studies—Example 5: A 78 year old female was presented with debilitating arthritis in both ankles. She had pain at rest, and was ambulatory primarily in a wheelchair, with minimal ability to stand or walk with a walker. She used various NSAIDs and prescription anti-pain narcotics daily. The patient was administered 700 mg (350 mg. glucosamine sulfate; 150 mg.curcumin; 150 mg. Milk thistle; 50 resveratrol) conjugate once a day for a month. She obtained symptom relief from arthritis, which included decreased pain and increased mobility without the use of a wheelchair or a walker. She discontinued the use of the narcotics. Side effects—none noted Clinical Case Studies—Example 6: A 28 year old white female was presented with a history of anxiety and lack of concentration. The patient was administered 700 mg (350 mg. glucosamine sulfate; 150 mg. curcumin; 150 mg. Milk thistle; 50 resveratrol) conjugate once a day for two weeks with moderate relief of symptoms of anxiety and reported increased ability to concentrate on normal work activities. Side effects—none noted Clinical Case Studies—Example 7: 62 year old male was presented with a history of moderate arthritis in left shoulder. The patient was administered 700 mg (350 mg. glucosamine sulfate; 150 mg.curcumin; 150 mg. Milk thistle; 50 resveratrol) conjugate once a day for two weeks with moderate relief of symptoms from the arthritis in the left shoulder. He could resume normal day to day work activities. Side effects—transient headache.

Clinical Animal Case Studies—Example 1: A 6 year old Golden Retrieve 90lb spayed female was presented lameness and lethargy associated with right shoulder arthritis and hip dysplasia. The animal was given 350 mg (175 mg. glucosamine sulfate; 75 mg.curcumin; 75 mg. Milk thistle; 25 resveratrol) conjugate in the feed once a day for two weeks. The dog resumed normal behavior and significant relief from pain associated with the arthritis. Side effects—none noted.

Clinical Animal Case Studies—Example 2: A 5 year old TB mare was presented with osteoarthritis in both hocks. It showed pain on flexion of each hock and "rough gait" at gallop. It was orally administered 10 grams (4900 mg. glucosamine sulfate; 2100 mg. curcumin; 2100 mg. Milk Thistle; 700 mg resveratrol) conjugate in the feed twice a day. After one week, the horse showed marked decrease in pain on flexion of hocks and smooth gait at gallop, along with calming and decrease anxiety. There was no adverse side effect.

Clinical Animal Case Studies—Example 3: A 2 year old mix breed 30lb spayed female displayed exercise induced lumbar vertebral trauma with moderate pain and lethargy. The dog was administered 175 mg. (90 mg chondroitin sulfate; 36 mg curcumin; 36 mg milk thistle; 13 mg resveratrol) conjugate orally once a day for one month. The dog resumed normal activities without any signs of associated back pain and lethargy.

The Whey-protein isolates that have been treated with curcumin ((1E,6E)-1,7-bis(4hydroxy-3-methoxyphenyl) hepta-1,6-diene-3,5-dione). The analytical procedure set out was to monitor the concentration of free curcumin and its metabolite tetrahydrocurcumin (THC) 1,7-Bis(4-hydroxy-3-methoxyphenyl)-3,5-heptanedione) in plasma from treated rats.

Mobile Phase-THC was (60% acetonitrile, 0.2% Ammonium hydroxide in water). To a clean glass bottle, transfer 600 mL of acetonitrile, 398 mL of USP water, and 2 mL of Ammonium hydroxide and mix well. The solution can be stored at room temperature for up to 1 month. Mobile Phase A was (0.1% Formic Acid in Water. To a clean, glass bottle, transfer 999 mL of USP purified water and 1 mL of formic acid (≥98% purity), and mix well. The solution can be stored at room temperature for up to 1 month. Mobile Phase B (0.1% Formic Acid in Acetonitrile). To a clean, glass bottle, transfer 999 mL of Acetonitrile, and 1 mL of formic acid (≥98% purity), and mix well. The solution can be stored at room temperature for up to 1 month. Needle Wash Solution 1 and 2, and Reconstitution Solution (60% Acetonitrile in Water). To a clean, glass bottle, transfer 400 mL of USP Purified Water, and 600 mL of Acetonitrile, and mix well. The solution can be stored at room temperature up to 1 month. 0.5M $NaH_2PO_4$ was made by Weigh approximately 27.6 g of Sodium Phosphate Monobasic, Monohydrate (MW: 137.99). Transfer the weighed reagent to a clean glass bottle and add 400 mL of USP Purified Water to dissolve it. Mix well. The solution may be stored at room temperature for up to 1 month.

Preparation of Stock Solutions: Stock solutions of Curcumin and Tetrahydrocurcumin were provided by Nucro-Technics at 1500 m/mL each in acetonitrile. Stock solutions of Curcumin-d6 and Tetrahydrocurcumin-d6 were provided by Nucro-Technics as 100 m/mL each in acetonitrile. All stock solutions were stored at −80° C.±10° C. Working standard solutions were prepared as per as shown in Table 1. Solutions were used immediately or stored at −80° C.±10° C.

TABLE 1

Analyte working standard solutions

| Solution to be Prepared | | Solution to be Diluted | | | Vol. of Acetonitrile (μL) | Final Volume (μL) |
|---|---|---|---|---|---|---|
| Name | Conc. (μg/mL) | Name | Conc. (μg/mL) | Vol. (μL) | | |
| WS1 | 125; 62.5 | SSA | 1500; N/A | 40 | 420 | 480 |
| | | SSB | N/A; 1500 | 20 | | |
| WS2 | 12.5; 6.25 | WS1 | 125; 62.5 | 20 | 180 | 200 |

TABLE 1-continued

| Analyte working standard solutions | | | | | | |
|---|---|---|---|---|---|---|
| Solution to be Prepared | | Solution to be Diluted | | | Vol. of Acetonitrile (μL) | Final Volume (μL) |
| Name | Conc. (μg/mL) | Name | Conc. (μg/mL) | Vol. (μL) | | |
| WS3 | 1.25; 0.625 | WS2 | 12.5; 6.25 | 20 | 180 | 200 |
| WS4 | 0.5; 0.25 | WS3 | 1.25; 0.625 | 40 | 60 | 100 |

Preparation of Internal Standard Solutions. WIS was prepared by diluting the 100 μg/mL Cucumin-d6 and Tetrahydrocurcumin-d6 internal standard stock solutions to 1000 ng/mL Cucumin-d6 and 500 ng/mL Tetrahydrocurcumin-d6 respectively in Reconstitution solution. Solution was used immediately or stored at −80° C.±10° C.

Preparation of Calibration standards and Quality Controls. Calibration standards were prepared from analyte working standard solutions as indicated in Table 2. Matrix (EDTA-treated Rat Male Plasma—Bioreclaimation IVT #RATPLEDTA2-M) was acidified using phosphoric acid to 5% (v/v). Calibration standard samples and QC samples were prepared in parallel with test samples and were injected after sample preparation (outlined in next section).

Sample extraction procedure. De-conjugated Rat plasma samples were provided by toxicology and stored at −80° C.±10° C. Plasma was thawed with protection from ambient light at room temperature. For each test sample, Calibration Standard, and QC sample, 1004 of each was pipetted into pre-labeled tubes. 400 μL of 0.5M NaH2PO4 was added to all tubes and tubes were vortexed adequately. 1004 of WIS was added to all tubes using a repeater pipette.

Samples were loaded onto ISOLUTE SLE+1 mL SPE cartridges and allowed to flow through. Samples were allowed to adsorb into packing for 10 minutes. Cartridges were eluted with 6 mL of MTBE into glass tubes applied as two 3 mL aliquots. Liquid was evaporated at 40° C. under nitrogen flow. 2504 of Reconstitution Solution was added to all tubes, vortexed adequately, and transferred to autosampler vials. Samples were kept at 6° C. in autosampler prior to same-day injection onto LC-MS Acquisition and Post-Acquisition data analysis. All 'unknown' samples were bracketed with calibration standard samples. Instrument response was integrated peak areas to appropriate MS internal standard compounds. Responses for each compound were tabulated and a calibration curves for Curcumin and THC were assembled using Xcalibur LCquan software.

TABLE 1

Calculations for Curcumin in test articles

| Dose Group | | Subgroup | Time | Rat | Response | Response Ratio | Calculated Conc. (ng/mL) |
|---|---|---|---|---|---|---|---|
| 1. | Curcumin Whey Powder Mixture | A | 30 min | 001 | 104339 | 0.01264 | 31.257 |
| | | | | 002 | 47015 | 0.00675 | 16.838 |
| | | B | 1 h | 003 | 66718 | 0.00949 | 23.552 |
| | | | | 004 | 47446 | 0.00593 | 14.849 |
| | | A | 2 h | 001 | 49823 | 0.00673 | 16.808 |
| | | | | 002 | 52832 | 0.00623 | 15.577 |
| | | B | 6 h | 003 | 8710 | 0.00111 | 3.042* |
| | | | | 004 | 7256 | 0.00106 | 2.912* |
| 2. | Curcumin powder | A | 30 min | 005 | 47605 | 0.00624 | 15.606 |
| | | | | 006 | 13255 | 0.00164 | 4.344* |
| | | B | 1 h | 007 | 25822 | 0.00279 | 7.150* |
| | | | | 008 | 28667 | 0.00330 | 8.390* |
| | | A | 2 h | 005 | 17611 | 0.00226 | 5.845* |
| | | | | 006 | 37712 | 0.00488 | 12.261 |
| | | B | 6 h | 007 | 5087 | 0.00071 | 2.068* |
| | | | | 008 | 5675 | 0.00070 | 2.036* |

*below LLQC

Results of THC Determination. Instrument responses for calibration curve and QC for THC are provided in Tables 6-7. The calibration curve which was fit with a quadratic model ignoring the origin. Results and calculations for the Curcumin content of test articles are shown in the Table 8.

TABLE 2

Calculations for THC in test articles

| Dose Group | | Subgroup | Time | Rat | Response | Response Ratio | Calculated Conc. (ng/mL) |
|---|---|---|---|---|---|---|---|
| 1. | Curcumin Whey Powder Mixture | A | 30 min | 001 | 263 | 0.00259 | 2.247* |
| | | | | 002 | 118 | 0.00141 | 1.586* |
| | | B | 1 h | 003 | 101 | 0.00116 | 1.450* |
| | | | | 004 | 189 | 0.00192 | 1.874* |
| | | A | 2 h | 001 | 128 | 0.00151 | 1.645* |
| | | | | 002 | 85 | 0.00092 | 1.312* |
| | | B | 6 h | 003 | NF | NA | NC |
| | | | | 004 | NF | NA | NC |
| 2. | Curcumin powder | A | 30 min | 005 | 471 | 0.00459 | 3.562* |
| | | | | 006 | 82 | 0.00087 | 1.289* |
| | | B | 1 h | 007 | 103 | 0.00103 | 1.375* |
| | | | | 008 | 126 | 0.00125 | 1.500* |
| | | A | 2 h | 005 | 106 | 0.00120 | 1.472* |
| | | | | 006 | 136 | 0.00147 | 1.620* |
| | | B | 6 h | 007 | 65 | 0.00071 | 1.194* |
| | | | | 008 | 82 | 0.00086 | 1.280* |

*below LLQC;
NF-non found;
NA-not applicable;
NC-not calculated

The main test articles in this study consist of Whey-protein isolates that have been treated with a Curcuminoid complex, which is comprised of curcumin (70-80%), demethoxy curcumin (15%-25%) and bisdemethoxycurcumin (2.5%-6.5%). As the nature of the interaction between major component, curcumin and whey-protein isolate is unclear, the determination of organic-extractable curcumin is desired which will provide an indirect indication for the amount of curcumin that has been adsorbed to the whey-protein isolate.

The analytical procedure set out was to monitor the amount of curcumin that could be extracted from the supplied whey-protein isolates by a targeted LC-MS/MS method.

Extraction Solution—Acetonitrile: Methanol: Formic Acid (80:19:1) by volume. Stock dilution solution—80% Acetonitrile: 0.1% Formic Acid by volume. Mobile Phase—50% Acetonitrile: 0.1% Formic Acid by volume.

Analyzed samples include: 1: Whey Protein Isolate, 2: Whey Protein/Curcumin preparation.—50 mg/g, 3: Whey Protein/Curcumin preparation—high temperature—25 mg/g and 4: Curcumin.

Preparation of Stock Solutions. A stock solution of Curcumin was prepared from highly purified material provided by Nucro-Technics to be used as an analytical calibration standard. The stock solutions were dissolved in DMSO at the following concentrations:

| Compound | MW | Stock Concentration | Notes |
|---|---|---|---|
| Curcumin | 368.38 g/mol | 5 mM | Nucro-Technics Standard (>97%) |
| Glyoxal-bis (2-hydroxyanil) | 240.26 g/mol | 24 mg/mL | MS internal standard |

Stock Solutions were stored at −80° C. ± 10° C.

Spiking Solution Preparation. A spiking solution (Spiking Solution A) was prepared in stock dilution solution (80% Acetonitrile: 0.1% Formic acid). The final concentration of Spiking Solution A was as follows: Final Concentration of Curcumin in Spiking solution A 25 µM A two-fold dilution series was prepared using Spiking Solution A with stock dilution solution to produce Spiking Solutions B through J to cover the analytical range of Curcumin.

| Calibration Level | Volume of Stock Dilution Solution in tube (µL) | Volume if Spiking solution transferred to this tube and mixed (µL) | Curcumin Final Concentration (µL) |
|---|---|---|---|
| Spiking Solution A | — | 500 | 25 |
| Spiking Solution B | 500 | 500 | 12.5 |
| Spiking Solution C | 500 | 500 | 6.25 |
| Spiking Solution D | 500 | 500 | 3.125 |
| Spiking Solution E | 500 | 500 | 1.563 |
| Spiking Solution F | 500 | 500 | 0.7813 |
| Spiking Solution G | 500 | 500 | 0.3906 |
| Spiking Solution H | 500 | 500 | 0.1953 |
| Spiking Solution I | 500 | 500 | 0.09766 |
| Spiking Solution J | 500 | 500 | 0.04883 |

After transferring, each spiking solution was mixed well.

Calibration Standards and QC Preparation. Calibration standards were prepared from the spiking solution, the MS internal standard, and Mobile Phase solution. The MS internal standard concentration was chosen based on its response during method development. The MS internal standard stock—Glyoxal-bis (2-hydroxyanil), 24 mg/mL—was diluted 1:5,000 in Mobile Phase solution for use as a 10× working stock solution.

Spiked standards were inverted by hand for 5-10 seconds. Each pool was then mixed by vortexing for 60 seconds. Pools were labeled and stored at −80° C.±10° C.

| Calibration Level | Curcumin Final Concentration of injectable (µM) | Vol Spiking Solution Added (µL) | Vol of MS internal standard added (µL) | Vol of mobile phase added (µL) | Total vol. (µL) |
|---|---|---|---|---|---|
| STD A | 1 | 20 | 50 | 430 | 500 |
| STD B | 0.5 | 20 | 50 | 430 | 500 |
| STD C | 0.25 | 20 | 50 | 430 | 500 |
| STD D | 0.125 | 20 | 50 | 430 | 500 |
| STD E | 0.0625 | 20 | 50 | 430 | 500 |
| STD F | 0.03125 | 20 | 50 | 430 | 500 |
| STD G | 0.01563 | 20 | 50 | 430 | 500 |
| STD H | 0.007813 | 20 | 50 | 430 | 500 |
| STD I | 0.003906 | 20 | 50 | 430 | 500 |
| STD J | 0.001953 | 20 | 50 | 430 | 500 |
| Blank | 0 | 0 | 50 | 450 | 500 |
| Double Blank | 0 | 0 | 0 | 500 | 500 |

| QC Level | Curcumin Final Concentration of injectable (μM) | Vol Spiking Solution Added (μL) | Vol of Matrix* added (μL) | Vol of MS internal standard added (μL) | Volume of Mobile Phase added (μL) | Total volume (μL) |
|---|---|---|---|---|---|---|
| QC High | 0.5 | 20 (Spiking solution B) | 100 | 50 | 330 | 500 |
| QC Med | 0.0625 | 20 (Spiking solution E) | 100 | 50 | 330 | 500 |
| QC Low | 0.007813 | 20 (Spiking solution H) | 100 | 50 | 330 | 500 |

*The matrix used for QC samples was 100 μL of supernatant from untreated Whey-protein isolate.

Extraction Procedure. Test Article 1, Test Article 2, Test Article 3 were accurately weighed (~100 mg of each). Test Article 4 was accurately weighed (~5 mg). Each was put into labeled 15 mL polypropylene screw-capped tubes. Extraction solution (5 mL) was added to each tube and vortexed vigorously for 30 seconds. Suspensions were allowed to sit in the dark at RT for 30 minutes to allow extraction and protein precipitation to occur. Tubes were centrifuged for 2000×g for 5 minutes at RT. Supernatant was removed (1 mL) to 1.5 mL microfuge tubes and subjected to centrifugation at 20,000×g for 30 minutes at 6° C. Supernatant was removed and stored at −80° C. Supernatant from step 4 was diluted 1:100 in duplicate for each test article into Stock Dilution solution. Samples for injection for test articles were prepared: 10 μL 1:100 diluted supernatant from step 5+50 μL MS Internal Standard+440 μL Mobile Phase (total volume: 500 μL). All Sample tubes including prepared standards and QC samples were centrifuged at 20,000×g for 5 min at 6° C. Supernatant (200 μL) was transferred into a polypropylene autosampler plate and analyzed by LC/MS/MS (10 μL injections of each). Note: Unknown test article samples were injected twice and different times during the sample sequence. Calibration standards were injected multiple times as brackets around unknown samples. QC samples and blanks were injected at different points during sample sequence to measure any effects of carry-over.

Results and Interpretation Curcumin Determination. Instrument responses for calibration curve and QC curve are provided in Table 9 and Table 10. The calibration curve which was fit with a quadratic model ignoring the origin. Results and calculations for the Curcumin content of test articles is shown in Table 11.

TABLE 9

Calibration curve data for Curcumin

| Calibration Level | Specified Concentration (μM) | Response | Response Ratio (to MS Int Std) | Back Calculated Concentration (μM) | % Difference | % RSD | % CV |
|---|---|---|---|---|---|---|---|
| A | 1 | 17804178 | 4.52424 | 1.006 | 0.59 | 1.37 | 1.31 |
|   |   | 17477326 | 4.49273 | 0.999 | −0.14 |   |   |
|   |   | 18384698 | 4.41069 | 0.98 | −2.05 |   |   |
| B | 0.5 | 9553838 | 2.27291 | 0.494 | −1.21 | 1.19 | 1.16 |
|   |   | 9658406 | 2.30265 | 0.501 | 0.12 |   |   |
|   |   | 10170571 | 2.25004 | 0.489 | −2.22 |   |   |
| C | 0.25 | 5005950 | 1.1894 | 0.256 | 2.21 | 1.62 | 1.6 |
|   |   | 5080612 | 1.19111 | 0.256 | 2.36 |   |   |
|   |   | 5134669 | 1.15758 | 0.249 | −0.56 |   |   |
| D | 0.125 | 2574889 | 0.6069 | 0.129 | 3.47 | 1.06 | 1.05 |
|   |   | 2662834 | 0.61886 | 0.132 | 5.53 |   |   |
|   |   | 2724043 | 0.60897 | 0.13 | 3.83 |   |   |
| E | 0.0625 | 1294205 | 0.30379 | 0.064 | 2.72 | 2.05 | 2.02 |
|   |   | 1297076 | 0.30922 | 0.065 | 4.58 |   |   |
|   |   | 1345161 | 0.29697 | 0.063 | 0.38 |   |   |
| F | 0.03125 | 654786 | 0.15415 | 0.032 | 2.94 | 1.15 | 1.12 |
|   |   | 648177 | 0.15135 | 0.032 | 1.02 |   |   |
|   |   | 677686 | 0.15106 | 0.032 | 0.83 |   |   |
| G | 0.01563 | 323361 | 0.07582 | 0.015 | −1.23 | 3.07 | 2.93 |
|   |   | 331331 | 0.07686 | 0.016 | 0.19 |   |   |
|   |   | 360156 | 0.08018 | 0.016 | 4.72 |   |   |
| H | 0.007813 | 168790 | 0.03893 | 0.008 | −3.15 | 5.21 | 4.74 |
|   |   | 165401 | 0.03941 | 0.008 | −1.84 |   |   |
|   |   | 162555 | 0.03607 | 0.007 | −10.96 |   |   |
| I | 0.003906 | 81955 | 0.01917 | 0.003 | −14.14 | 1.29 | 1.05 |
|   |   | 81709 | 0.01889 | 0.003 | −15.69 |   |   |
|   |   | 91938 | 0.02076 | 0.004 | 88.97 |   |   |
| J | 0.001953 | 44131 | 0.01024 | 0.001 | −25.87 | 54 | 39.7 |
|   |   | 46356 | 0.01056 | 0.002 | −22.3 |   |   |
|   |   | 45666 | 0.01049 | 0.002 | −23.1 |   |   |

TABLE 10

QC sample data for Curcumin

| QC Level | Specified Concentration (μM) | Response | Response Ratio (to MS Int Std) | Back Calculated Concentration (μM) | % Difference | % RSD | % CV |
|---|---|---|---|---|---|---|---|
| High | 0.5 | 8107909 | 2.34762 | 0.511 | 2.12 | 0.66 | 0.64 |
|  |  | 8104125 | 2.37389 | 0.516 | 3.29 |  |  |
| Medium | 0.0625 | 1037969 | 0.29641 | 0.063 | 0.18 | 2.36 | 2.33 |
|  |  | 1077488 | 0.30635 | 0.065 | 3.59 |  |  |
| Low | 0.007813 | 145761 | 0.04182 | 0.008 | 4.75 | 6.61 | 6.04 |
|  |  | 136858 | 0.0384 | 0.007 | −4.61 |  |  |

TABLE 11

Calculations for Curcumin in test articles

| Test Article | Replicate | Injection | Response | Response Ratio (to MS Int Std) | Sample dilution factor (from 5 mL organic extract) | Calculated Concentration (μM) in the 5 mL organic extract | Curcumin in 5 mL organic extract (mg) | Mean (mg) | Std Dev | Original Test article Weighed for extraction (mg) | % of original Test Article by weight |
|---|---|---|---|---|---|---|---|---|---|---|---|
| 1 | 1 | 1 | 6085* | 0.0015 | 5000 | 0 | 0 | 0 | — | 99.9 | — |
|  |  | 2 | 9107* | 0.00218 | 5000 | 0 | 0 |  |  |  |  |
|  | 2 | 1 | 5224* | 0.00126 | 5000 | 0 | 0 |  |  |  |  |
|  |  | 2 | 3094* | 0.00074 | 5000 | 0 | 0 |  |  |  |  |
| 2 | 1 | 1 | 5150104 | 1.24409 | 5000 | 1335 | 2.459 | 2.530 | 0.1021 | 100.5 | 2.5% |
|  |  | 2 | 5181937 | 1.2346 | 5000 | 1325 | 2.441 |  |  |  |  |
|  | 2 | 1 | 5290790 | 1.2928 | 5000 | 1390 | 2.560 |  |  |  |  |
|  |  | 2 | 5325111 | 1.34102 | 5000 | 1445 | 2.662 |  |  |  |  |
| 3 | 1 | 1 | 1301617 | 0.32125 | 5000 | 340 | 0.626 | 0.626 | 0.0130 | 100.1 | 0.63% |
|  |  | 2 | 1243747 | 0.31355 | 5000 | 330 | 0.608 |  |  |  |  |
|  | 2 | 1 | 1251658 | 0.32398 | 5000 | 345 | 0.635 |  |  |  |  |
|  |  | 2 | 1310155 | 0.32835 | 5000 | 345 | 0.635 |  |  |  |  |
| 4 | 1 | 1 | 6554050 | 1.60788 | 5000 | 1735 | 3.196 | 3.219 | 0.0555 | 5.008 | 64% |
|  |  | 2 | 6302833 | 1.61644 | 5000 | 1745 | 3.214 |  |  |  |  |
|  | 2 | 1 | 6430208 | 1.65946 | 5000 | 1790 | 3.297 |  |  |  |  |
|  |  | 2 | 6666139 | 1.5932 | 5000 | 1720 | 3.168 |  |  |  |  |

*below detection limit

Interpretation for Curcumin Determination for Test Articles. For Test Item 2, the calculated organic-extractable curcumin as percent by weight of the original test article was 2.5%. Test Item 2 was prepared as containing 5% by weight of Test Item 4 (a curcuminoid complex) which based on our analysis of the curcuminoid complex contains 64% curcumin. Thus, Test Item 2 should contain 3.2%, but only 2.5% was recovered. This would suggest that 22% of the total curcumin is unaccounted for assuming that 100% of the curcumin was extractable by our method. This fraction of curcumin that is unaccounted could be a combination of degradation of curcumin from formulation in the Test Item or incomplete extraction of curcumin from the Test Item. While incomplete extraction could be due to insufficient organic solvent used, and would need to be investigated, this explanation is unlikely as curcumin is readily soluble in various polar organic solvents. Thus it may likely that curcumin has been at least partially adsorbed (very tightly bound or covalently linked) to the whey-protein isolate in the Test Item. Test Item 3 was calculated to have 0.63% by weight of organic-extractable curcumin. Test Article 3 was formulated with 2.5% by weight of Test Item 4, thus it should contain 1.6% by weight of curcumin. As this formulation underwent heating during preparation, there is the possibilty that some curcumin was lost during this step. Additional reasons, for the difference between the curcumin that should be present in Test Item 3 and what was measured would be the same as those raised for Test Article 2. Test Article 4 was calculated to contain 64% by weight of curcumin and is within range of the supposed concentration (70-80%) for curcumin in curcumin complex.

Results and Interpretation for Demethoxycurcumin and Bisdemethoxycurcumin. Since demethoxycurcumin and bisdemethoxycurcumin are components of the original curcuminoid complex, an attempt was made to detect these components in Test Items 2 and 4. As they were easily detectable in these Test items, they were optimized for fragmentation in the mass spectrometer and were measured by MRM using LC-MS/MS similar to curcumin. The important differences are that no calibration curve was used for demethoxycurcumin and bisdemethoxycurcumin.

In Table 12 and Table 13, the results for bisdemethoxycurcumin and demethoxycurcumin and are presented. There is a calculation for the ratio of the ratios of response between bisdemethoxycurcumin or demethoxycurcumin and Curcumin. This should only be considered a rough estimate of ratio between the compounds as they are not corrected using heavy isotope-labeled internal standards for each compound. Nonetheless, the percentages calculated are close to their reported content in the curcuminoid complex.

TABLE 12

Response for Bisdemethoxycurcumin in Test Articles

| Test Article | Replicate | Injection | Response | Response Ratio (to MS Int Std) | Ratio of Response ratios Bis dimethoxy curcumin: Curcumin | Mean |
|---|---|---|---|---|---|---|
| 1 | 1 | 1 | 2286* | 0.00056 | — | |
| | | 2 | 2208* | 0.00053 | — | |
| | 2 | 1 | 1975* | 0.00048 | — | |
| | | 2 | 1285* | 0.00031 | — | |
| 2 | 1 | 1 | 122931 | 0.0297 | 2.39 | 2.22 |
| | | 2 | 123213 | 0.02936 | 2.38 | |
| | 2 | 1 | 106189 | 0.02595 | 2.01 | |
| | | 2 | 112485 | 0.02833 | 2.11 | |
| 3 | 1 | 1 | 58944 | 0.01455 | 4.53 | 4.51 |
| | | 2 | 62658 | 0.0158 | 5.04 | |
| | 2 | 1 | 54875 | 0.0142 | 4.38 | |
| | | 2 | 53513 | 0.01341 | 4.08 | |
| 4 | 1 | 1 | 287430 | 0.07051 | 4.39 | 4.41 |
| | | 2 | 283275 | 0.07265 | 4.49 | |
| | 2 | 1 | 275836 | 0.07119 | 4.29 | |
| | | 2 | 297199 | 0.07103 | 4.46 | |

*below detection limit

TABLE 13

Response for Demethoxycurcumin in Test Articles

| Test Article | Replicate | Injection | Response | Response Ratio (to MS Int Std) | % Ratio of Response ratios Demethoxy curcumin: Curcumin | Mean % of Curcumin |
|---|---|---|---|---|---|---|
| 1 | 1 | 1 | 1510* | 0.00037 | — | |
| | | 2 | 1260* | 0.0003 | — | |
| | 2 | 1 | 1867* | 0.00045 | — | |
| | | 2 | 1763* | 0.00042 | — | |
| 2 | 1 | 1 | 917312 | 0.22159 | 17.81 | 18.05 |
| | | 2 | 930972 | 0.2218 | 17.97 | |
| | 2 | 1 | 976266 | 0.23855 | 18.45 | |
| | | 2 | 957214 | 0.24106 | 17.98 | |
| 3 | 1 | 1 | 318279 | 0.07855 | 24.45 | 25.42 |
| | | 2 | 322849 | 0.08139 | 25.96 | |
| | 2 | 1 | 319002 | 0.08257 | 25.49 | |
| | | 2 | 337224 | 0.08451 | 25.74 | |
| 4 | 1 | 1 | 1774018 | 0.43521 | 27.07 | 27.25 |
| | | 2 | 1701003 | 0.43624 | 26.99 | |
| | 2 | 1 | 1742916 | 0.4498 | 27.11 | |
| | | 2 | 1855329 | 0.44342 | 27.83 | |

*below detection limit

Results for Pepsin digestion and mass spectrometry of Test Articles 1, 2, and 3. After initial dissolution to 10 mg/mL in 0.1% formic acid, all test articles appears to be colloidal indicating a lack of solubility at this concentration. Centrifugation resulted in a compact pellet in each case along with clear supernatant. The supernatant for Test article 1 was colourless while Test articles 2 and 3 had bright yellow supernatants. A protein assay was performed on the supernatants and is shown in Table 14 and is indicative of a saturated solution in 0.1% formic acid in which each solution contained equal amounts of protein (~1 mg, Table) for pepsin digestion and mass spectrometry.

TABLE 14

Results of Protein assay of Supernatant for Pepsin Digestion

| Test Article | Mean Protein (mg/mL) in 0.1% formic acid | Amount of protein treated with Pepsin (mg) |
|---|---|---|
| 1 | 5.968 | 1.194 |
| 2 | 5.374 | 1.075 |
| 3 | 5.656 | 1.131 |

Protein Search results. The top-ranking proteins identified (10 or more assigned peptide spectra) in the test articles according to number of peptide assigned are shown in Table 15. While there are no major differences in the protein identifications between the test articles, it was noted that Test Article 3 had far fewer peptides assigned to the identified proteins. This could be due to the heat-treatment of Test Article 3 causing protein modifications that are not accounted for during the peptide matching, or due to a stochastic event during the mass spectrometry (only one injection of each pepsin-digested test articles was performed). Modification of any amino acid for the mass of curcumin and its theoretical covalently modified species (368.13, 370.40, and 352.00) were added to detect potential modifications or adducts. This modification was assigned to few low scoring peptides for some proteins identified in Test Articles 1 and 2 indicating that assignments could be non-specific as Test Article 1 did not contain curcumin.

fold (see report). While many of these changes are due to variations in the alignment between the runs, there are several that may represent peptides that are modified by the curcumin treated. It is anticipated that the most specific changes would be represented by 1) appearance of a new feature in Test Article 2—representing the modified peptide, and 2) a decrease in intensity of a feature in Test Article 2 compared with Test Article 1—representing the fraction of the material that is modified as it is unlikely that the modification will occur for all peptides.

In vitro studies, Characterization of the Curcumin Whey Protein Mixture: The "free curcumin" content of the conjugate in reference to the curcumin whey protein mixture will be determined by extracting the curcumin whey protein

TABLE 15

Proteins identified in Test Articles with >10 spectra

| Identified Proteins | Accession Number | Molecular Weight | Number of Assigned Spectra | | |
|---|---|---|---|---|---|
| | | | Test Article 1 | Test Article 2 | Test Article 3 |
| Major allergen beta-lactoglobulin OS = Bos taurus PE = 2 SV = 1 | B5B0D4_BOVIN | 20 kDa | 357 | 447 | 95 |
| Beta-casein OS = Bos taurus GN = CSN2 PE = 1 SV = 2 | CASB_BOVIN | 25 kDa | 128 | 150 | 37 |
| Glycosylation-dependent cell adhesion molecule 1 OS = Bos taurus GN = GLYCAM1 PE = 1 SV = 2 | GLCM1_BOVIN | 17 kDa | 108 | 121 | 42 |
| Serum albumin OS = Bos taurus GN = ALB PE = 1 SV = 4 | ALBU_BOVIN | 69 kDa | 51 | 42 | 0 |
| Alpha-lactalbumin protein variant D OS = Bos taurus GN = LALBA PE = 3 SV = 1 | G9G9X6_BOVIN (+1) | 16 kDa | 42 | 43 | 0 |
| Kappa-casein OS = Bos taurus GN = CSN3 PE = 1 SV = 1 | CASK_BOVIN | 21 kDa | 0 | 40 | 0 |
| Alpha-S1-casein OS = Bos taurus GN = CSN1S1 PE = 1 SV = 2 | CASA1_BOVIN | 25 kDa | 43 | 55 | 0 |
| Alpha-S2-casein OS = Bos taurus GN = CSN1S2 PE = 1 SV = 2 | CASA2_BOVIN | 26 kDa | 36 | 44 | 0 |
| Uncharacterized protein (Fragment) OS = Bos taurus PE = 1 SV = 1 | G3N0V0_BOVIN | 36 kDa | 26 | 25 | 0 |
| Putative uncharacterized protein OS = Bos taurus PE = 2 SV = 1 | A5D7Q2_BOVIN | 52 kDa | 14 | 21 | 0 |
| Osteopontin OS = Bos taurus GN = SPP1 PE = 1 SV = 2 | OSTP_BOVIN (+1) | 31 kDa | 15 | 15 | 0 |
| Polymeric immunoglobulin receptor OS = Bos taurus GN = PIGR PE = 2 SV = 1 | PIGR_BOVIN | 82 kDa | 0 | 15 | 0 |
| Alpha-1-acid glycoprotein OS = Bos taurus GN = ORM1 PE = 2 SV = 1 | A1AG_BOVIN (+1) | 23 kDa | 14 | 13 | 0 |
| Butyrophilin subfamily 1 member A1 OS = Bos taurus GN = BTN1A1 PE = 1 SV = 2 | BT1A1_BOVIN | 59 kDa | 15 | 16 | 0 |
| Transthyretin OS = Bos taurus GN = TTR PE = 1 SV = 1 | TTHY_BOVIN | 16 kDa | 0 | 11 | 0 |

Comparison using Progenesis QI for Proteomics. As the potential modification of peptides with curcumin remains undefined, a comparison between Test Articles 1 and 2 was made that is independent of protein identification and peptide assignments. For this comparison, the retention time versus the m/z pattern of each run was compared using Progenesis QI for Proteomics (Demo licence; Non-Linear Dynamics) with the assumption that a curcumin modification will change the retention time and the mass-to-charge ratio (m/z) of the peptide. An overview of both runs demonstrates that the majority of 'features'—molecules detected by the mass spectrometer—are very similar between the samples. The software detected over 21,000 features, with over 1,700 showing abundance changes of greater than 500 mixture and raw curcumin powder into an organic solvent and measuring the levels of curcumin using an LC-MS based method. The potential for the binding of curcumin covalently to the whey protein will be investigated by subjecting the conjugate and whey protein to enzyme digestion and evaluating peptide fragments in comparison to a digested sample of the whey protein alone using an LC-MS method to determine the nature of the fragments and comparatively if any of the fragments have curcumin bound to them. When complete, these studies will clarify the nature of the test material as to its content of either free curcumin or covalently linked curcumin or both. These studies will be critical to evaluation of the critical analytes to be searched for when conducting in vivo studies in rats which will include, curcumin, the metabolite tetrahydrocurcumin (THC), and curcumin or THC potentially bound to either a peptide or amino acid.

This study quantified the plasma levels of curcumin and THC following the dose of rats with curcumin powder and a curcumin whey protein conjugate following oral dosing at doses of 12 mg/kg and 240 mg/kg, respectively. In addition, two other components of the curcumin powder, demethoxy and bis-demethoxy curcumin were qualitatively analyzed.

Analysis of plasma levels of total curcumin and THC following the dosing of rats with curcumin powder and the curcumin whey protein complex resulted in only detectable levels (above the limit of quantification) being observed for curcumin. Curcumin was orally absorbed from both preparations rapidly with $T_{max}$ values of 0.5 hr. Plasma curcumin levels were higher following dosing with the curcumin whey protein complex compared to dosing with an equivalent dose of the curcumin powder alone. The $C_{max}$ and AUC0-∞ values were higher by 2.4-fold and 2.0-fold for the curcumin whey protein complex compared to the powder, respectively. Oral clearance and volume of distribution were high and comparatively lower (by 2.0-fold and 2.5-fold, respectively) for curcumin derived following dosing with the whey protein complex compared to the powder; the oral clearance values were consistent with the literature.

The plasma peak areas for demethoxycurcumin and bis-demethoxycurcumin identified at their masses showed a similar profile of increase and decrease when compared to curcumin. The peak areas at each time point were similar between the demethoxy and bis-demethoxy following dosing with the curcumin whey protein complex and the curcumin powder suggesting a similar absorption of these components from the two oral preparations. In conclusion, plasma curcumin levels were higher in rats orally dosed with curcumin whey protein complex compared to oral dosing with curcumin powder alone by ~2-fold.

The objective of this study was to measure the plasma levels of total curcumin and its metabolite tetrahydrocurcumin (THC) following dosing with a curcumin Whey protein conjugate and for comparison, an equivalent dose of curcumin powder in Sprague Dawley rats. Two other components of the curcumin powder, demethoxycurcumin and bis-demethoxycurcumin were qualitatively evaluated. Tissue distribution was to be studied only if substantial plasma levels of curcuminoids were found in the plasma.

Curcumin Whey Protein Conjugate. An appropriate amount of curcumin whey protein conjugate was weighed and to which was added a solution of 0.5% w/v Methyl Cellulose in sterile water for injection 0.1% v/v Tween-80 (v/v) such that the final concentration of the curcumin whey protein conjugate was 24 mg/mL (and contained 1.2 mg/mL as curcumin). The mixture was vortexed and sonnicated for 10 seconds prior to being kept stirring at room temperature prior to dosing.

Curcumin Complex. An appropriate amount of curcumin complex was weighed and to which was added a solution of 0.5% w/v Methyl Cellulose in sterile water for injection 0.1% v/v Tween-80 (v/v) such that the final concentration of the curcumin complex was 1.2 mg/mL. The mixture was vortexed and sonnicated for 10 seconds prior to being kept stirring at room temperature prior to dosing.

Species: *Rattus norvegicus*; Strain: CD® [Crl:CD®(SD) BR] (Sprague-Dawley); Source: Charles River Canada Inc., Montreal, PQ; Total No. of Animals on Study: 8 Males; No. of Study Groups: 2; No. of Animals per Group: 4; Body Weight: 314.0-328.3 g at start of dosing; Age: 10-13 weeks at start of dosing; Acclimatization Period: 10 days.

Animal Housing, Identification and Maintenance/Environment. Male rats were used for this study. The animals were housed individually in Nalgene® rat cages, and were identified with a unique permanent marking. The animal number and group number also appeared on a color-coded card attached to the outside of each animal's cage. The animal room environment was controlled (targeted ranges: temperature 18-26° C., relative humidity 30-70%, greater than 10 air changes/hour) and monitored. The photo-cycle was 12 hours light and 12 hours dark. The cage cleaning schedule, air filtration and recirculation, health checks and facility maintenance were carried out in accordance with the applicable Nucro-Technics' Standard Operating Procedures and such activities were recorded in the animal room records. Diet/Water. Teklad Certified Rodent Diet (#8728C) and municipal water were provided to the animals. It is considered that there were no known contaminants in the animals' diet or water that might have influenced the outcome of this study. Animal Welfare. The testing facility complied with all local regulations governing the care and use of laboratory animals. Procedures are designed to avoid or minimize discomfort, distress and pain to the rats in accordance with the principles of the Ontario Animals For Research Act (RSO 1990, Chapter A.22); Guide for the Care and Use of Laboratory Animals, 8th Edition, NRC, 2011; and the Guidelines of Canadian Council on Animal Care (CCAC). The CCAC Guide for the Care and Use of Experimental Animals and reacted polices and the AAALAC Guide for the Care and Use of Laboratory Animals, were regarded as the guidelines to follow. The testing facility has a certificate of registration as a research facility under the Animals for Research Act issued by the Ontario Ministry of Agriculture and Food and is accredited in Good Animal Practices® by the CCAC and AAALAC.

Dosing of Rats. Male Rats were orally dosed with the curcumin whey protein conjugate and the curcumin complex according to the study design in Table 16.

TABLE 16

Study Design

| Dose Group | Dose (mg/kg) | Dose Volume (mL/kg) | Concentration (mg/mL) | No. and Sex of animals per time point |
|---|---|---|---|---|
| Curcumin Whey Powder Mixture | 240 | 10 | 24 | Subgroup A 2M Subgroup B 2M |
| Curcumin Powder | 12 | 10 | 1.2 | Subgroup A 2M Subgroup B 2M |

M denotes male rats

Blood samples 0.6-0.8 mL were taken according to the schedule below at 0.5, 1, 2 and 6 hrs postdosing as described in Table 17 into tubes containing K2EDTA.

Organ/tissue collection was performed following the last bleed at 2 and 6 hours as described in Table 18. The following organs/tissues were collected: brain, kidneys, major lobes of the lung and liver, pancreas and one whole joint of the knee and ankle combined. The organs were homogenized in 5 volumes per gram wet-weight of 0.5 M $NaH_2PO_4$, using three 5-second bursts of a polytron. The resulting homogenates were frozen (at −80±10° C.) pending possible analysis.

Plasma was separated by centrifugation, the plasma isolated and maintained in the dark at 2-8° C. Following collection of all plasma samples, they were treated with deconjugating enzymes (glucuronidase and sulfatase) to remove conjugation of curcumin in the form of glucuronides and sulfates. Briefly, a 120 μL aliquot of plasma was treated with 10% of the plasma volume of 50 mM sodium phosphate buffer, pH 7.4 (for optimal enzymatic pH). Subsequently, 60 μL of an enzymatic mix containing 5000 Units/mL of β-glucuronidase and 100 Units/mL of sulfatase, dissolved in 0.1 M sodium acetate, pH 5.5+0.1% BSA (w/v) was added to the tubes. The tubes were incubated at 37° C. for 30 minutes, to which was subsequently added 5% v/v of phosphoric acid following which the samples were frozen at −80±10° C. until analyzed. Duplicate samples were taken at each time point.

TABLE 17

Blood Sampling Schedule

| Dose Group | No. and Sex of animals per time point | Blood collection | | | |
|---|---|---|---|---|---|
| | | 0.5 hr | 1 hr | 2 hrs | 6 hrs |
| Curcumin Whey Powder Mixture | Subgroup A 2M | √ | | √ | |
| | Subgroup B 2M | | √ | | √ |
| Curcumin Powder | Subgroup A 2M | √ | | √ | |
| | Subgroup B 2M | | √ | | √ |

TABLE 18

Organ Collection

| Dose Group | No. and Sex of animals per time point | Organ/Tissue Collection | |
|---|---|---|---|
| | | 2 hrs | 6 hrs |
| 1. Curcumin Whey Powder Mixture | Subgroup A 2M | √ | |
| | Subgroup B 2M | | √ |
| Curcumin Powder | Subgroup A 2M | √ | |
| | Subgroup B 2M | | √ |

Rats were observed for any untoward effects of dosing with the conjugate.

Sample Analysis. Initially, plasma samples were analyzed for curcumin and THC by LC/MS-MS using methods described. In addition, a qualitative analysis of the two remaining curcuminoids in the curcumin complex, demethoxy- and bis-demethoxty curcumin was performed. These two compounds were measured using an LC-MS/MS method used in study no. 312730 and analyzed separately from the primary assay of curcumin and THC. After supplying the client with a preliminary report on the plasma levels of total curcumin, a decision was taken not to analyze the tissue samples for free levels of curcumin and THC at this time.

Pharmacokinetic Analysis. Plasma concentration-time data for curcumin was analyzed by the non-compartmental method to obtain the pharmacokinetic parameters using validated PHOENIX® WINNONLIN® version 6.3 software (Pharsight Corp).

The main parameters were calculated: AUC0-Tlast: Area under the plasma concentration-time curve from time zero to the time of the last quantifiable concentration at time Tlast, calculated using the linear trapezoidal rule. AUC0-∞: Area under the plasma concentration curve from time zero extrapolated to infinity AUC0-∞ will be calculated as AUC0-Tlast+(Clast/ke). $C_{max}$: Maximum plasma concentration. $T_{max}$: Time of maximum concentration determined from the nominal time of blood sampling. Kel: Elimination rate constant. This will be estimated using linear regression on the terminal phase of the semi-logarithmic concentration-time curve. A minimum of three data points will be used for the calculation of ke. No weighting will be applied to the regression line. t½: Terminal elimination half-life calculated from ln(2)/kel. MRTobs: Mean residence time. CLoral: Oral clearance. Vzoral: Oral volume of distribution.

The individual plasma levels of total curcumin and THC are presented in Table 19 and the average plasma levels of curcumin and THC are not shown. The pharmacokinetic parameters calculated for curcumin are presented in Table 20. The peak areas representing the masses for the demethoxycurcumin and bis-demethoxycurcumin components of the curcumin powder are not shown. The oral dosing of either curcumin powder or curcumin powder whey protein complex was well tolerated by rats. Analysis of plasma levels of total curcumin and THC following the dosing of rats with curcumin powder and the curcumin whey protein complex resulted in only detectable levels (above the limit of quantification) being observed for curcumin. For the analysis of the pharmacokinetic parameters of curcumin, both plasma levels above and below the limit of quantification were employed. Curcumin was orally absorbed from both preparations rapidly with $T_{max}$ values of 0.5 hr. Plasma curcumin levels were higher following dosing with the curcumin whey protein complex compared to dosing with an equivalent dose of the curcumin powder alone. The $C_{max}$ and AUC0-∞ values were higher by 2.4-fold and 2.0-fold for the curcumin whey protein complex compared to the powder, respectively. Oral clearance and volume of distribution were high and comparatively lower (by 2.0-fold and 2.5-fold, respectively) for curcumin derived following dosing with the whey protein complex compared to the powder. The magnitude of the oral clearance for curcumin observed in this study is consistent with that observed previous studies, where an oral clearance of 108.5 L/kg/hr for curcumin was observed.

Given the low levels of THC observed, a pharmacokinetic analysis was not performed. However, the levels were quite similar following dosing with the curcumin whey protein complex and the powder. Although quantification of the demethoxy and bis-demethoxy curcumin components of the complex was not undertaken, the plasma peak areas identified at their masses showed a similar profile of increase and decrease when compared to curcumin. The peak areas at each time point were slightly less and similar for the demethoxy and bis-demethoxy, respectfully, when comparing dosing with the curcumin whey protein complex and the curcumin powder, suggesting more or less similar absorption of these components from the two oral preparations.

The data from this study was compared to a literature study in which two powder forms of curcumin were orally administered to rats either as curcumin powder alone or curcumin powder in a capsule formulation; each form of curcumin was dosed to rats at 100 mg/kg and plasma levels of total curcumin (free, glucuronidated and sulfated) determined up to 2 hrs post-dosing. Normalization of the AUC0-2 hr for the two dose forms (AUC in ng-hr/mL/Dose in mg/kg) resulted in values of 2.3 for curcumin powder and 3.2 for curcumin in the capsule. In the current study, the AUC0-2 hrs for total curcumin (deconjugated) for the curcumin powder was 26.31 ng-hr/mL and for the curcumin whey protein complex was 56.7 ng-hr/mL. Since curcumin is ~75% curcumin, the actual dose of curcumin was 9 mg/kg as opposed to 12 mg/kg as the complex. Normalization of the total curcuminoid AUC0-2 hrs from this study to the dose of curcumin lead to values of 2.9 for the curcumin powder and 6.3 for the curcumin whey protein complex. The dose normalized values for the AUC0-2 hrs of total curcuminoids for the curcumin powder are in excellent agreement with the literature, while the value for the curcumin powder whey protein complex suggests that it can deliver more curcumin systemically compared to curcumin powder alone.

TABLE 19

Total Curcumin and THC Found in Rat Plasma Samples

| Dose Group | Subgroup | Time (hr) | Rat | Curcumin Concentration (ng/mL) | THC Concentration (ng/mL) |
|---|---|---|---|---|---|
| 1. Curcumin Whey Powder Complex | A | 0.5 | 001 | 31.257 | 2.247* |
|  |  |  | 002 | 16.838 | 1.586* |
|  | B | 1 | 003 | 23.552 | 1.450* |
|  |  |  | 004 | 14.849 | 1.874* |
|  | A | 2 | 001 | 16.808 | 1.645* |
|  |  |  | 002 | 15.577 | 1.312* |
|  | B | 6 | 003 | 3.042* | NC |
|  |  |  | 004 | 2.912* | NC |
| 2. Curcumin Powder | A | 0.5 | 005 | 15.606 | 3.562* |
|  |  |  | 006 | 4.344* | 1.289* |
|  | B | 1 | 007 | 7.150* | 1.375* |
|  |  |  | 008 | 8.390* | 1.500* |
|  | A | 2 | 005 | 5.845* | 1.472* |
|  |  |  | 006 | 12.261 | 1.620* |
|  | B | 6 | 007 | 2.068* | 1.194* |
|  |  |  | 008 | 2.036* | 1.280* |

*below LLQC; NC—not calculated, no peak found

TABLE 20

Pharmacokinetic Parameters for Curcumin in Rats Dosed With Curcumin Whey Protein Complex and Curcumin Powder

| Group | $C_{max}$ (ng/mL) | $T_{max}$ (hr) | $AUC_{0-Tlast}$ (ng-hr/mL) | $AUC_{0-\infty}$ (ng-hr/mL) | $K_{el}$ (hr$^{-1}$) | $R^1$ | AUC Extrapolation (%) | $t_{1/2}$ (hr) | MRTobs (hr) | $CL_{oral}$ (L/kg/hr) | $Vz_{oral}$ (L/kg) |
|---|---|---|---|---|---|---|---|---|---|---|---|
| Curcumin | 16.8 | 0.5 | 59 | 71 | 0.307 | 0.99 | 16 | 2.3 | 3.2 | 128 | 416 |
| Whey | 40.4 | 0.5 | 131 | 145 | 0.375 | 0.93 | 9 | 1.8 | 2.5 | 62 | 166 |

The elimination pharmacokinetic parameters for curcumin were based on regression of three plasma concentration time points between 1 and 6 hrs post dosing and past the Cmax concentration. [1]Coefficient of linear regression for determination of Kel, the terminal phase elimination rate constant.

Acute Dosing, Pharmacokinetics and Tissue Distribution of a Curcumin-Whey Protein Conjugate. (i) Male Rats will be orally dosed with the curcumin whey protein mixture (as a suspension in 0.5% Methocel or formulation designed by the Client) at a human total daily equivalent (60 kg human at 2.4 g/day, 40 mg/kg) rat dose of 240 mg/kg and for comparison the equivalent of the curcumin powder (95%, Curcumin complex) used to prepare the conjugate, also suspended in 0.5% methocel according to the study design in Table 21.

TABLE 21

| Study Design | | | | |
|---|---|---|---|---|
| Dose Group | Dose (mg/kg) | Dose Volume (mL/kg) | Concentration (mg/mL) | No. and Sex of animals per time point |
| Curcumin Whey Powder Mixture | 240 | 10 | 24 | Subgroup A 2M<br>Subgroup B 2M |
| Curcumin Powder | 12 | 10 | 1.2 | Subgroup A 2M<br>Subgroup B 2M |

M denotes male rats

Blood samples 0.6-0.8 mL will be taken according to the schedule below at 0.5, 1, 2 and 6 hrs postdosing as described in Table 22 into tubes containing $K_2EDTA$.

Organ/tissue collection will be done performed following the last bleed at 2 and 6 hours as described in Table 23. The following organs/tissues will be collected: brain, kidneys, major lobes of the lung and liver, pancreas and either the whole joint or the articular cartilage of the knee (and/or ankle or both). The organs will be homogenized in 5 volumes per gram wet-weight of 0.5 M $NaH_2PO_4$, using three 5-second bursts of a polytron. The resulting homogenate will be frozen (at $-80\pm10°$ C.) pending analysis.

Plasma will be separated by centrifugation, the plasma isolated and maintained in the dark at 2-8° C. Following collection of all plasma samples, they will be treated with deconjugating enzymes (glucuronidase and sulfatase) to remove conjugation in the forms of glucuronides and sulfates. Briefly, a 120 μL aliquot of plasma will first be treated with 10% of the plasma volume of 50 mM sodium phosphate buffer, pH 7.4 (for optimal enzymatic pH). Subsequently, 60 μL of an enzymatic mix containing 5000 Units/mL of β-glucuronidase and 100 Units/mL of sulfatase, dissolved in 0.1 M sodium acetate, pH 5.5+0.1% BSA (w/v) will be added to the tubes. The tubes will be incubated at 37° C. for 30 minutes, to which will be subsequently added 5% v/v of phosphoric acid following which the samples will be frozen at $-80\pm10°$ C. until analyzed. Duplicate samples will be taken at each time point. Total curcumin and THC in the plasma will be quantificated by LC-MS. Potential non-conjugated plasma curcumin metabolites will be identified by performing metabolite scanning by LC-MS and reported. Quantification of any of the metabolites will be dependent on the availability reference standards.

TABLE 22

Blood Sampling Schedule

| Dose Group | No. and Sex of animals per time point | Blood collection | | | |
| --- | --- | --- | --- | --- | --- |
| | | 0.5 hr | 1 hr | 2 hrs | 6 hrs |
| 1. Curcumin Whey Powder Mixture | Subgroup A 2M | √ | | √ | |
| | Subgroup B 2M | | √ | | √ |
| Curcumin Powder | Subgroup A 2M | √ | | √ | |
| | Subgroup B 2M | | √ | | √ |

TABLE 23

Organ Collection

| Dose Group | No. and Sex of animals per time point | Organ/Tissue Collection | |
| --- | --- | --- | --- |
| | | 2 hrs | 6 hrs |
| 1. Curcumin Whey Powder Mixture | Subgroup A 2M | √ | |
| | Subgroup B 2M | | √ |
| Curcumin Powder | Subgroup A 2M | √ | |
| | Subgroup B 2M | | √ |

Rats were be observed for any untoward effects of dosing with the conjugate.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

What is claimed is:

1. A pharmaceutical polyphenol complex comprising
   a therapeutically effective amount of one or more polyphenols disposed in a pharmaceutically acceptable carrier, wherein the one or more polyphenols comprises quercetin; and
   one or more complexing agents conjugated to the one or more polyphenols in a ratio of one or more polyphenols to one or more complexing agents of between about 1:2 and 1:20, wherein the one or more complexing agents are amino sugars.

2. The composition of claim 1, wherein the one or more polyphenols are non-covalently conjugated to the one or more complexing agent.

3. The composition of claim 1, wherein the one or more polyphenols comprise 2, 3, 4, 5, 6, or more polyphenols.

4. The composition of claim 1, wherein the one or more complexing agents comprise N-acetylglucosamine, glucosamine sulfate or N-acetylgalactosamine, glucuronic acid, iduronic acid, galactose chondroitin and glucosamine, glycosaminoglycan Chondroitin sulfate, fucoidan or Glucosamine sulfate.

5. A nutraceutical composition comprising
   a therapeutically effective amount of one or more polyphenols disposed in a pharmaceutically acceptable carrier, wherein the one or more polyphenols comprises quercetin; and
   one or more complexing agents conjugated to the one or more polyphenols in a ratio of one or more polyphenols to one or more complexing agents of between about 1:2 and 1:20, wherein the one or more complexing agents are amino sugars.

* * * * *